(12) United States Patent
Henley et al.

(10) Patent No.: US 10,119,104 B2
(45) Date of Patent: Nov. 6, 2018

(54) METHODS OF MAKING PERSONAL CARE ARTICLES

(71) Applicant: The Procter & Gamble Company, Cincinnati, OH (US)

(72) Inventors: Eric Shane Henley, West Harrison, IN (US); William Allen Watters, North College Hill, OH (US); Darren Franklin King, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 54 days.

(21) Appl. No.: 15/455,240

(22) Filed: Mar. 10, 2017

(65) Prior Publication Data

US 2018/0258374 A1 Sep. 13, 2018

(51) Int. Cl.
*A61K 8/02* (2006.01)
*C11D 17/04* (2006.01)
*C11D 3/37* (2006.01)
*A61Q 19/10* (2006.01)

(52) U.S. Cl.
CPC .......... *C11D 17/041* (2013.01); *C11D 3/3749* (2013.01); *A61K 8/0208* (2013.01); *A61K 2800/87* (2013.01); *A61Q 19/10* (2013.01); *C11D 17/049* (2013.01)

(58) Field of Classification Search
CPC .... C11D 17/049; A61Q 19/10; A61K 8/0208; A61K 2800/87
USPC ........................................ 15/104.93; 510/439
See application file for complete search history.

(56) References Cited

U.S. PATENT DOCUMENTS

| | | | |
|---|---|---|---|
| 6,491,928 B1 | 12/2002 | Smith | |
| 7,381,693 B2 | 6/2008 | Keenan et al. | |
| D752,883 S | 4/2016 | Althaus et al. | |
| D765,327 S | 8/2016 | Althaus et al. | |
| 9,554,978 B2 | 1/2017 | McConaughy et al. | |
| 2003/0231922 A1 | 12/2003 | Kudalkar et al. | |
| 2004/0009030 A1 | 1/2004 | Kudalkar et al. | |
| 2004/0242097 A1* | 12/2004 | Hasenoehrl ........ | A44B 18/0011 442/59 |
| 2006/0246119 A1 | 11/2006 | Eknoian et al. | |
| 2012/0246851 A1* | 10/2012 | Smith, III ................ | A61Q 5/02 15/104.93 |
| 2012/0246852 A1 | 10/2012 | Smith et al. | |

(Continued)

FOREIGN PATENT DOCUMENTS

WO WO00/78611 A2 12/2000
WO WO03/099985 A2 12/2003

*Primary Examiner* — Gregory E Webb

(57) ABSTRACT

A method of making a personal care article includes placing a converting frame on an anvil plate assembly with an anvil plate; placing at least one lower substrate on the anvil plate and the converting frame; securing the at least one lower substrate within the converting frame; placing a cleansing composition on the at least one lower substrate and within a perimeter of a centering guide on the anvil plate; laying at least one upper substrate over the cleansing composition and the at least one lower substrate; placing the converting frame and the anvil plate assembly on a target location of a heat press; and actuating the heat press to direct a heated seal plate onto the anvil plate, thereby contacting the at least one upper substrate and forming seal between the at least one upper substrate and the at least one lower substrate.

20 Claims, 9 Drawing Sheets

(56) References Cited

U.S. PATENT DOCUMENTS

| | | | |
|---|---|---|---|
| 2013/0043147 A1* | 2/2013 | Smith, III | A61Q 19/00 206/38 |
| 2015/0000522 A1 | 1/2015 | Ahn et al. | |
| 2015/0005223 A1* | 1/2015 | McConaughy | A61K 8/42 510/439 |
| 2016/0128912 A1 | 5/2016 | McConaughy et al. | |
| 2016/0130021 A1 | 5/2016 | McConaughy et al. | |

* cited by examiner

METHODS OF MAKING PERSONAL CARE ARTICLES

FIELD

The present application is directed to methods of making personal care articles.

BACKGROUND

Cleansing is an activity that has been done for many years. Over time, cleansing has involved the use of compositions such as bar and liquid soaps, body washes, shampoos, conditioners, liquid and/or solid detergents, and the like. For these compositions, consumers desire good cleansing properties and lathering characteristics, mildness toward the target surface, like skin, fabric, or hard surface, and the ability to provide benefit agents to the target surface.

Some cleansing has been done with rigid cleansing compositions, like bar soap. These rigid forms may be difficult for the consumer to handle, especially when wet. Also, they are difficult to use directly on the target area for cleansing as the contact surface area of the bar soap is limited by the shape of the target surface.

Coupling rigid and liquid cleansing compositions with implements, such as a washcloth, a sponge, or a puff, is also known. For example, many consumers dispense liquid soaps or body washes onto a puff and then cleanse by applying the puff to their skin and/or hair. Similarly, many consumers rub bar soaps with a washcloth and then cleanse by applying the washcloth to their skin and/or hair. Additionally, many consumers apply cleansing compositions to sponges to clean hard surfaces. However, such experiences have not been completely ideal. For example, such experience may require the user to perform additional steps (e.g., applying the body wash or soap on the implement), and possibly, consume more product as a result. Such experiences may lead to clutter in the kitchen, shower, or bath as a consumer needs to carry or store cumbersome bottles, bars, jars, and/or tubes of cleansing products in addition to the implements. Further, certain personal cleansing compositions, such as bar soaps, may have difficulty providing the consumer with the desired deposition of benefit agents, even when coupled with an implement.

While some attempts have been made to combine an implement with a personal cleansing composition to provide an effective personal care article, it would be desirable, in some examples, to provide improved methods of making personal care articles, where such methods can improve efficiency and repeatability, reduce process times and waste, and enhance ergonomic aspects of the process, while ensuring the quality of the product.

SUMMARY

According to one example, a method of making a personal care article comprises placing a converting frame on an anvil plate assembly comprising an anvil plate; placing at least one lower substrate on the anvil plate and the converting frame; securing the at least one lower substrate within the converting frame; placing a cleansing composition on the at least one lower substrate and within a perimeter of a centering guide on the anvil plate; laying at least one upper substrate over the cleansing composition and the at least one lower substrate; placing the converting frame and the anvil plate assembly on a target location of a heat press; and actuating the heat press to direct a heated seal plate onto the anvil plate, thereby contacting the at least one upper substrate to form a seal between the at least one upper substrate and the at least one lower substrate and thereby contain the cleansing composition therebetween.

According to another example, a method of making a personal care article comprises placing a converting frame on an anvil plate assembly comprising an anvil plate; placing at least one lower substrate on the anvil plate and the converting frame; securing the at least one lower substrate within the converting frame; placing a cleansing composition on the at least one lower substrate and within a perimeter of a centering guide on the anvil plate; laying at least one upper substrate over the cleansing composition and the at least one lower substrate; placing the converting frame and the anvil plate assembly on a target location of a heat press; actuating the heat press to direct a heated seal plate onto the anvil plate, thereby contacting the at least one upper substrate to form a seal between the at least one upper substrate and the at least one lower substrate and thereby contain the cleansing composition between the at least one upper and lower substrates; separating the anvil plate assembly from the converting frame; placing the converting frame on a surface of a cutting press; placing a die assembly comprising a die over the at least one upper substrate on the converting frame, such that the die is facing the surface of the cutting press; and actuating the cutting press to drive the die assembly onto the converting frame to cut excess portions of the at least one lower substrate and the at least one upper substrate at or outwardly adjacent to the seal to form the personal care article.

According to another example, a method of making a personal care article comprises unitizing a plodded extrudate cleansing composition to form a cleansing composition puck; placing a converting frame on an anvil plate assembly comprising an anvil plate, placing at least one lower substrate on the anvil plate and the converting frame and securing the at least one lower substrate within the converting frame; placing the cleansing composition puck on the at least one lower substrate and within a perimeter of a centering guide on the anvil plate, wherein the centering guide is substantially visible through the at least one lower substrate; playing at least one upper substrate over the cleansing composition puck and the at least one lower substrate; placing the converting frame and the anvil plate assembly on a target location of a heat press, wherein a first physical guide facilitates placement of the converting frame and the anvil plate assembly on the target location of the heat press; actuating the heat press to direct a heated seal plate onto the anvil plate, thereby contacting the at least one upper substrate to form a seal between the at least one upper substrate and the at least one lower substrate and thereby contain the cleansing composition puck therebetween; separating the anvil plate assembly from the converting frame; placing the converting frame on a surface of a cutting press; placing a die assembly comprising a die over the at least one upper substrate on the converting frame, such that the die is facing the surface of the cutting press, wherein a second physical guide facilitates placement of the die assembly on the converting frame; and actuating the cutting press to drive the die assembly onto the converting frame to cut excess portions of the at least one lower substrate and the at least one upper substrate at or outwardly adjacent to the seal to form the personal care article and to shape the cleansing composition therein; where the die and the die assembly define a die cavity having a depth that is less than a height of the cleansing composition prior to actuation of the cutting press.

DETAILED DESCRIPTION OF THE INVENTION

Definitions

Figure 1:
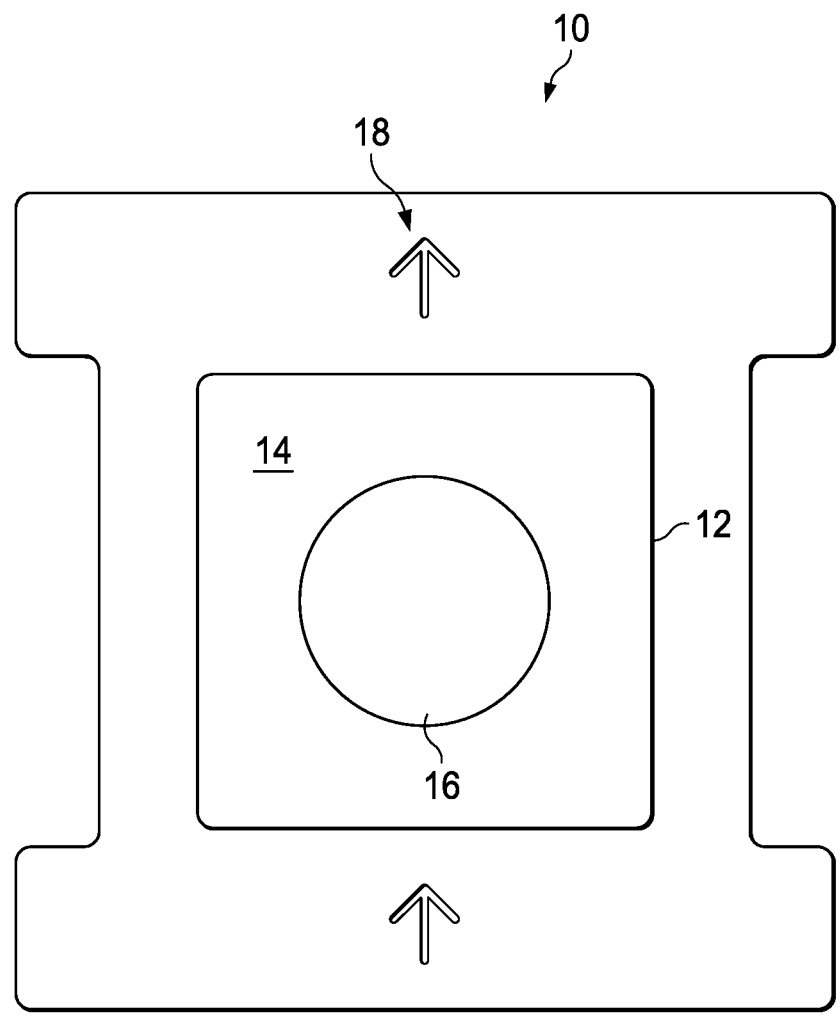
FIG. 1 depicts a top view of an anvil plate assembly with an anvil plate, according to one example.

As used herein, the following terms shall have the meaning specified thereafter:

"Cellulose" as used herein refers to cellulose in the form of fines, fibers, and/or filaments; and/or aggregates thereof.

"Compliant" as used herein refers to an article and/or composition with a compliance value of about 1.5 kg/mm or less as measured according to the Compliance Test set out below.

"Fiber" as used herein refers to an elongate particulate having an apparent length exceeding its apparent diameter, i.e. a length to diameter ratio of about 7 or more. Fibers having a non-circular cross-section and/or tubular shape are common; the "diameter" in this case may be considered to be the diameter of a circle having cross-sectional area equal to the cross sectional area of the fiber. "Fiber length", "average fiber length" and "weighted average fiber length", are terms used interchangeably herein all intended to represent the "Length Weighted Average Fiber Length". Fiber length and diameter can be measured in accordance with standard procedures and machinery, like a STFI FiberMaster available from Innventia AB, Sweden. The recommended method for measuring fiber length using this instrument is essentially the same as detailed by the manufacturer of the Fiber Master in its operation manual.

"Filament" as used herein refers to a combination of fibers and fines.

"Fine" as used herein refers to both primary and secondary fines (unless otherwise noted) which are water insoluble materials that pass through a 200 mesh screen under conditions defined in the TAPPI method T-261(80).

"g/use" refers to grams per use, which is the unit used for rate of consumption. The method for measuring and/or calculating the rate of consumption is described herein.

"Land area" is a generally flattened area existing within a plane and is generally impermeable, existing pores in that area are usually sealed off in the manufacturing process. While the land area is generally flat, there is no requirement that it be perfectly flat and it could itself contain some patterning. Patterning could include, for example, creating roughness in order to reduce the gloss of the substrate.

"Natural" as used herein refers to materials that can be derived from plants, animals, or insects, or materials that can be byproducts of plants, animals, or insects; excluding materials produced by bacteria.

"Personal care" refers to a composition or article for topical application to skin and/or hair. Personal care compositions or cleansing compositions, which may include rinse-off formulations, in which the cleansing composition may be applied topically to the skin and/or hair and then subsequently rinsed within seconds to minutes of application. Such cleansing compositions may be provided within a personal care article for topical application to the skin and/or hair.

"Pores" are holes in a substrate to allow passage of components such as water or other fluids, air or other gases and vapors, and/or material components such as surfactant or actives which may be dissolved or suspended in fluids.

"Reusable" refers to an article that may be used for a number of usage events, such as showers and/or baths, wherein the number of usage events may be about 5 or greater, about 7 or greater, about 10 or greater, about 15 or greater, about 20 or greater, about 25 or greater, or about 30 or greater.

"Simulated use" as used herein, refers to a simulated use as described in the Compliance Test below for measuring compliance after a simulated bath/shower, unless otherwise noted.

"Soft solid" as used herein refers to a compositional form which is viscoelastic, like a dough or a paste, and generally remains together as a single piece during use.

"Substrate" as used herein refers to a layer included within a personal care article that may enhance cleansing and therapeutic treatment of a surface such as skin and/or hair. The substrate may be water insoluble and/or water penetrable. The personal care article may comprise both water penetrable substrates and water impenetrable substrates. Suitable examples of substrates may include, for example, a formed film (e.g., a vacuum formed film), a nonwoven, a woven, a sponge, a batting, spunbond, spunlace, hydroentangled, carded, needlepunch, any other suitable material, or combinations thereof. In certain examples, the substrate may be a composite material that may include, for example, one or more plies of the same or different materials such as nonwovens, wovens, films, sponges, scrims, battings, and the like superimposed physically, joined together continuously (e.g., laminated, etc.) in a discontinuous pattern, or by bonding the substrate(s) at one or more locations such as, for example, at the external edges (or periphery) of the substrate and/or at discrete loci.

"Surface aberration" refers to a raised portion on a surface of a substrate which may be readily apparent to the naked eye and may form a pattern or design on a surface of a substrate. A surface aberration is not a pore or a protuberance.

"Unit cell" is a repeating geometrical pattern which may be measured along with the dimensions of the land and raised areas or structures within it in order to calculate the fractional amounts of land and raised areas for the substrate. A unit cell may be made up of, for example, surface aberrations, land area, and/or features.

"Usage event" refers to one cycle of the Consumption Test described below.

"Water insoluble" when used in relation to fines, fibers, or filaments, refers to those that do not substantially dissolve when placed in water at 42° C. for 15 minutes.

"Water insoluble substrate" refers to a substrate which does not dissolve before at least 10 simulated uses.

"Water penetrable substrate" refers to a substrate which allows water to pass through it into the personal care article and/or to the composition.

Methods of Making Personal Care Articles

Personal care articles may come in many forms. In one example, a personal care article may include two or more substrates (e.g., films) and a personal care composition (e.g., a compliant cleansing composition), where the substrates may be sealed to form, for example, a pouch, and the personal care composition may be contained therein.

While processes for making such articles are known, challenges exist in current processes for making personal care articles. As with any process, many of these challenges lie in improving efficiency and ergonomics. In particular, with respect to manual aspects of such processes, finding ways to reduce or eliminate human error and minimize the extent to which individual operators are responsible for the precision and accuracy involved in a certain task may greatly improve process times, repeatability, and product yield while reducing waste.

For example, while a heated plate may be used to provide a seal between two or more substrates, such substrates must be adequately secured and/or aligned prior to sealing to ensure, for example, that the plate fully contacts desired portions of the substrates, that the personal care article does not include any imperfections (e.g., undesirable wrinkles), or that the cleansing composition does not interfere with formation of the seal, among other concerns. As such, in some examples, ensuring that the task of adequately securing and/or aligning substrates prior to seal formation, among other tasks, is accurately and easily repeatable improves efficiency. One or more illustrative methods may allow for this and other tasks to be ergonomically and routinely performed.

It is believed that the one or more of the illustrative processes described in the present disclosure may provide such benefits. It is further believed that such processes may utilize one or more illustrative apparatuses described herein to effect improvements in efficiency and ergonomics. For example, the apparatuses may allow operators to more quickly perform steps while providing greater consistency therein.

Figure 2:
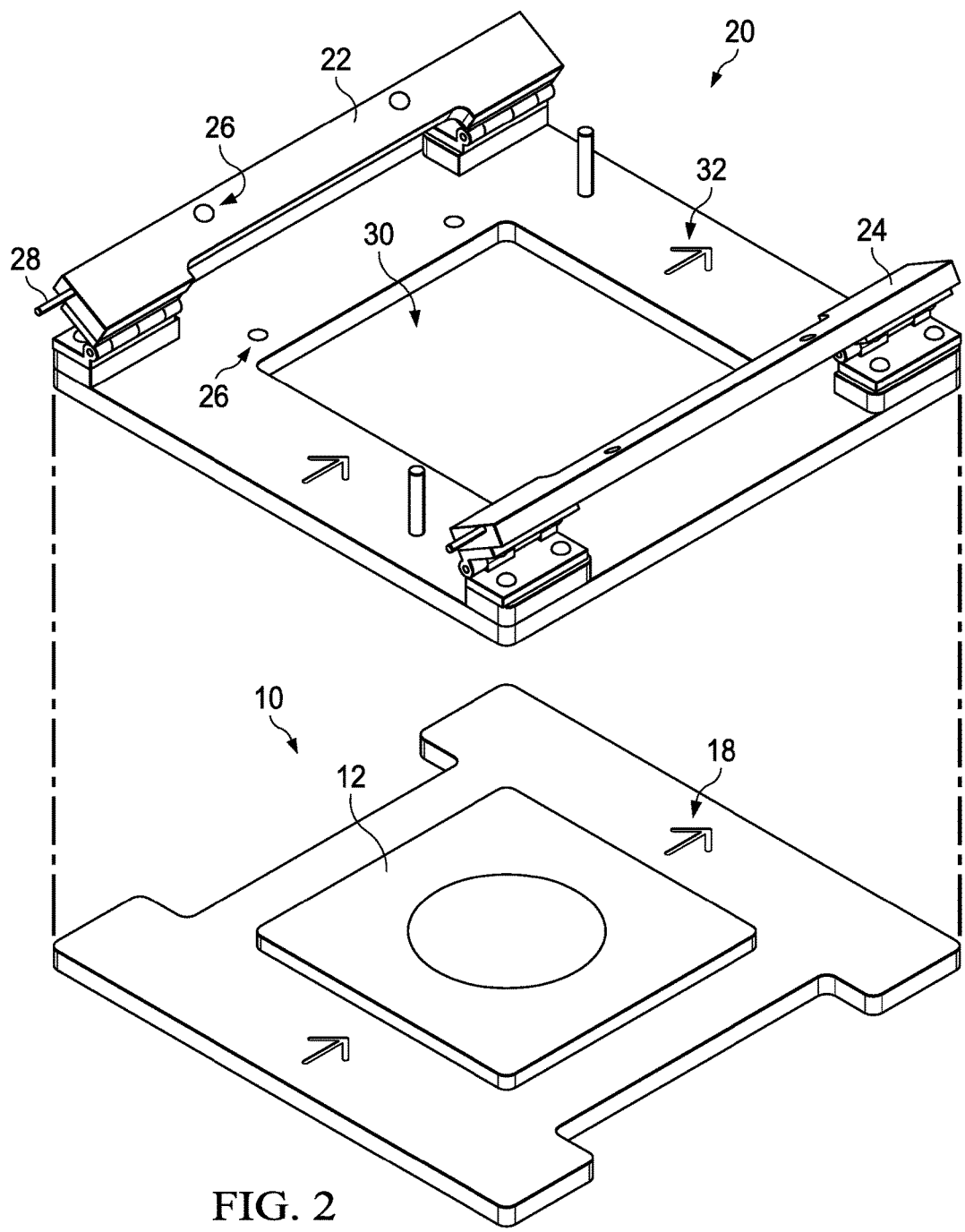
FIG. 2 depicts an isometric, exploded view of a converting frame over the anvil plate assembly of FIG. 1.

One such apparatus, an anvil plate assembly 10, is shown in FIG. 1. The anvil plate assembly 10 may include an anvil plate 12, which may be elevated from the rest of the anvil plate assembly 10, as best shown in FIG. 2. A top surface 14 of the anvil plate 12 may include a centering guide 16. While the anvil plate 12 and centering guide 16 are shown in FIG. 1 to have a square shape and a circular shape, respectively, it will be understood that both an anvil plate and a centering guide may have any of a variety of suitable shapes and configurations. In some examples, the anvil plate 12 may be formed from 90 A-durometer silicone. However, it will be appreciated that an anvil plate may be formed of any of a variety of suitable materials and at a wide range of hardness values, spanning the full Shore A and Shore D scales. In certain examples, the anvil plate may be formed from a silicone having a hardness value from about 40 A to about 100 A. In certain examples, the anvil plate 12 may include a metal surface (e.g., aluminum, steel). The anvil plate assembly 10 may further include one or more indicators to facilitate identification of a preferred orientation. In one example, the one or more indicators may be a set of arrows. In FIG. 1, for example, the anvil plate assembly 10 is shown to include a first set of arrows 18, with arrows positioned on opposite sides of the anvil plate 12 (e.g., opposite ends of the anvil plate assembly 10).

Another illustrative apparatus, a converting frame 20, is shown in FIG. 2. The converting frame 20 may include a first clamping wing 22 and a second clamping wing 24. Each of the first and second clamping wings 22, 24 may be hingedly attached to the converting frame 20, such the first and second clamping wings 22, 24 may be movable between an open position, as shown in FIG. 2, and a closed position shown in FIG. 5. To secure the first and second clamping wings 22, 24 in a closed position, one of a pair of magnetic clamps 26 may be included in each of the clamping wings (e.g., 22, 24) and the converting frame 20, such that the pair of magnetic clamps may be aligned in a closed position. In one example, the pair of magnetic clamps 26 may be embedded within the clamping wing (e.g., 22, 24) and the converting frame 20. One or more pairs of magnetic clamps 26 may be associated with each of the first and second clamping wings 22, 24. In one example, each of the first and second clamping wings 22, 24 may be associated with two pairs of magnetic clamps 26. In some examples, the converting frame and/or clamping wings may include other mechanisms to secure the clamping wings to the converting frame such as, for example, snap-fit connections, bolt connections, screw connections, protrusion/detent connections, or the like. In some examples, the clamping wings may be held secured to the converting frame by springs biasing the converting wings toward and engaged against the converting frame. Each of the first and second clamping wings 22, 24 may further include a knob 28, which may facilitate an operator's movement of the first and second clamping wings 22, 24 between the open position and the closed position. Though the first and second clamping wings 22, 24 are shown in FIG. 2 to be hingedly attached to the converting frame 20, it will be appreciated that a clamping wing may be attached to a converting frame in any of a variety of suitable configurations such that the clamping wing is movable between an open position and a closed position.

Figure 3:
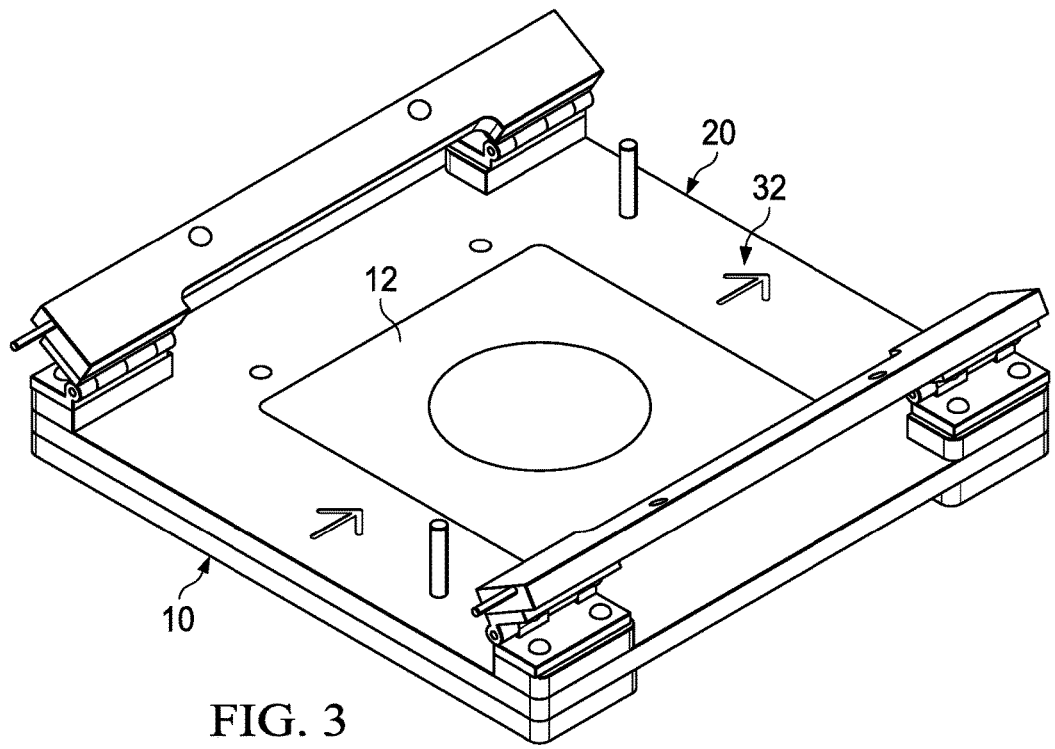
FIG. 3 depicts an isometric view of the converting frame and the anvil plate assembly of FIG. 2, where first and second clamping wings of the converting frame remain in an open position.

A method of making a personal care article may include placing the converting frame 20 over the anvil plate assembly 10, as shown, for example, in FIGS. 2 and 3. As best shown in FIG. 2, the converting frame 20 may define a window 30, which may be configured to receive the anvil plate 12 of the anvil plate assembly 10. In certain examples, and as shown, for example, in FIGS. 2 and 3, respective thicknesses of the converting frame 20 and the anvil plate 12 may be substantially similar such that, when the converting frame 20 and the anvil plate assembly 10 are in contact with each other (e.g., assembled together as shown in FIG. 3), upper surfaces of the converting frame 20 and the anvil plate 12 may form a substantially even upper surface. Similarly, in certain examples, the window 30 and the anvil plate 12 may be substantially similarly sized and shaped such that, when the converting frame 20 and the anvil plate assembly 10 are in contact with each other (e.g., assembled together as shown in FIG. 3), the window 30 may receive the anvil plate 12 to provide a fit that can minimize relative movement between the converting frame 20 and the anvil plate assembly 10, yet not hinder an operator's ability to separate the converting frame 20 and the anvil plate assembly 10 when necessary.

Like the anvil plate assembly 10, the converting frame 20 may further include one or more indicators to facilitate identification of a preferred orientation. As shown in FIG. 2, for example, the converting frame 20 may include a second set of arrows 32, with arrows positioned on opposite sides of the window 30 (e.g., opposite ends of the converting frame 20). In certain examples, an operator may be able to verify a desired alignment of the converting frame 20 over the anvil plate assembly 10 by aligning and/or matching the first set of arrows 18 with the second set of arrows 32 such that, for example, both the first and second sets of arrows 18, 32 are pointing in the same direction or orientation. In certain examples, one or both of the converting frame 20 and the anvil plate assembly 10 may be substantially transparent, such that an operator may be able to verify the desired alignment of the converting frame 20 over the anvil plate assembly 10 (e.g., by viewing through the converting frame 20 to see that the second set of arrows 32 are aligned or matched with the first set of arrows 18) while the converting frame 20 and the anvil plate assembly 10 are in contact with each other and/or assembled together.

Figure 4:
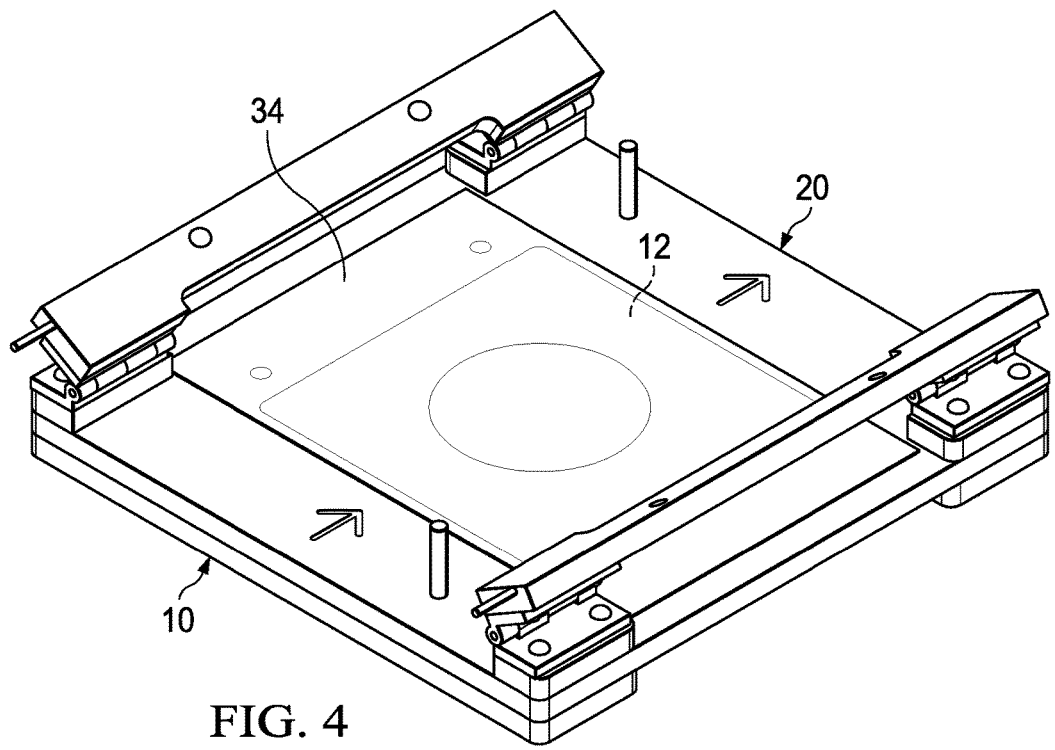
FIG. 4 depicts an isometric view of the converting frame and the anvil plate assembly of FIG. 3, with a lower film placed over the converting frame and anvil plate and where the first and second clamping wings remain in an open position.

The method of making a personal care article may further include placing at least one lower substrate (e.g., 34) on the anvil plate 12 and converting frame 20. In certain examples, and as shown in FIG. 4, the at least one substrate can include a lower film 34, which may be placed over the anvil plate 12 and converting frame 20. In one example, the lower film 34 may substantially cover the anvil plate 12. It will be appreciated, however, that in other examples, two or more lower substrates may be placed over an anvil plate and a converting frame. In one example, the at least one lower substrate may include two lower films, where a first lower film may be formed of polyethylene and a second lower film may include a textured surface such as, for example, a textured surface for scrubbing. When assembled, the first lower film may be positioned over the second lower film, such that the second lower film may be an outermost layer of the personal care article and the first lower film may separate the second lower film from the cleansing composition. Suitable examples of substrates and films are described herein below and in U.S. Patent Publication Nos. 2015/0000057, 2015/0000058, 2015/0005223, all published on Jan. 1, 2015.

Figure 5:
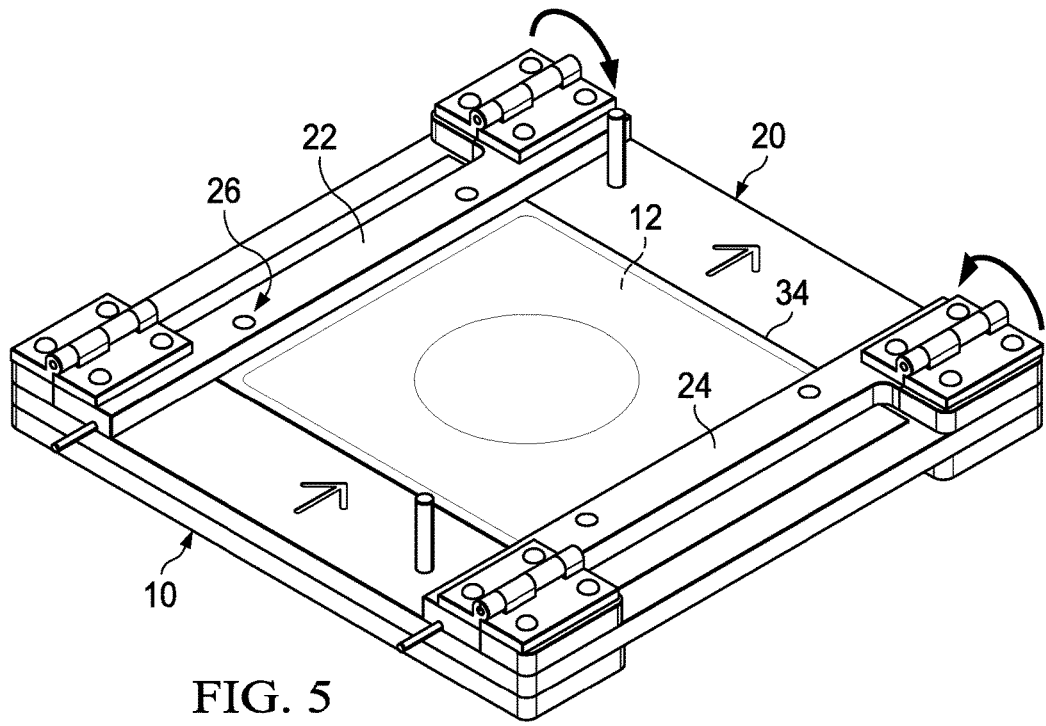
FIG. 5 depicts an isometric view of the converting frame, the anvil plate assembly, and the lower film of FIG. 4, where the first and second clamping wings are in a closed position, thereby securing the lower film within the converting frame.

The method of making a personal care article may further include securing the at least one lower substrate (e.g., 34) within the converting frame 20. In certain examples, and as shown in FIG. 5, once the lower film 34 has been placed over the anvil plate 12 and converting frame 20, the lower film 34 may be secured within the converting frame 20 by moving the first and second clamping wings 22, 24 to the closed position. Pairs of magnetic clamps 26 may become aligned in the closed position, as described above, such that magnetic forces between the pairs of magnetic clamps 26 may facilitate the securement of each of the first and second clamping wings 22, 24 to the converting frame 20, thereby securing the lower film 34 between the first and second clamping wings 22, 24 and the converting frame 20. In some examples, the at least one lower substrate (e.g., 34) may be secured between one or more pairs of magnetic clamps 26, where the magnetic forces between the pairs of magnetic clamps 26 may be strong enough to secure the each of the first and second clamping wings 22, 24 to the converting frame 20 through the at least one lower substrate (e.g., 34). It will be appreciated that while FIG. 5 shows pairs of magnets being employed to secure the lower film 34 within the converting frame 20, it will be appreciated that in other examples, any of a variety of suitable configurations may be employed to secure at least one lower substrate within a converting frame.

Figure 6:
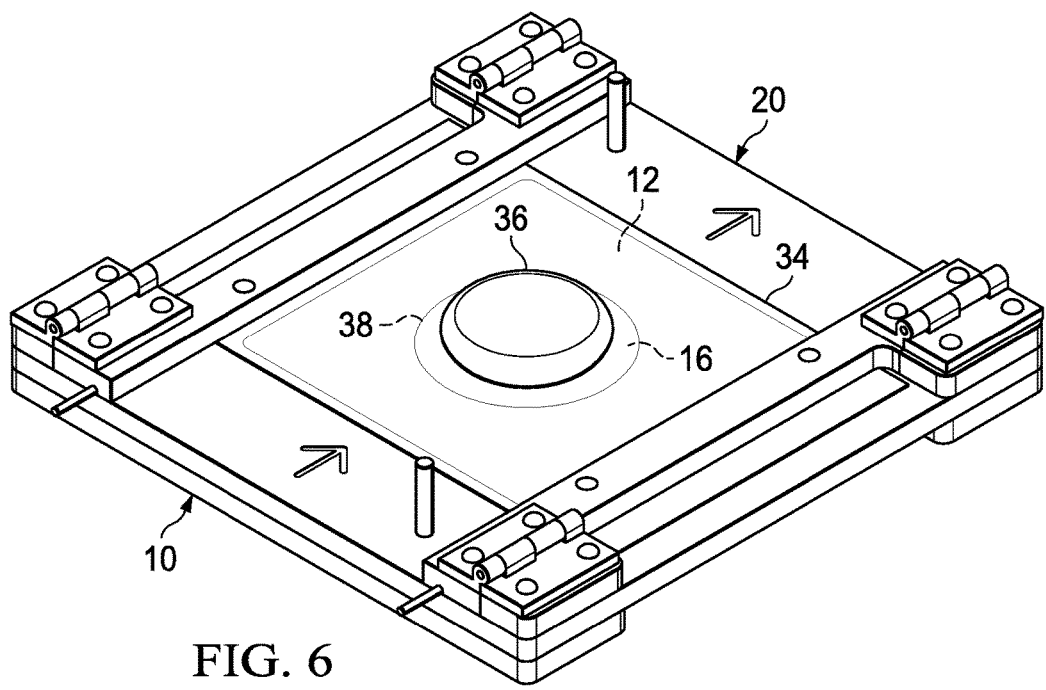
FIG. 6 depicts an isometric view of the converting frame, the anvil plate assembly, and the lower film of FIG. 5, with a cleansing composition puck placed over the lower film and where the first and second clamping wings remain in a closed position.

The method of making a personal care article may further include placing a cleansing composition (e.g., a cleansing composition puck 36) on the at least one lower substrate (e.g., 34) and within a perimeter 38 of a centering guide 16 on the anvil plate 12. In certain examples, the centering guide 16 may correspond to a two-dimensional zone in which a cleansing composition (e.g., 36) may avoid interference with a seal plate of a heat press, at least with respect to the two dimensions represented by the centering guide 16. In one example, and as shown in FIG. 6, the centering guide 16 on the anvil plate 12 may be configured such that it is visible through the at least one lower substrate (e.g., 34).

In certain examples, the cleansing composition (e.g., 36) may comprise a surfactant and a water insoluble hygroscopic fiber, fine, or filament. In one example, a surfactant (e.g., cocamidopropyl betaine) may be combined with preservatives in a tank equipped with an impeller mixing blade. Other surfactants (e.g., sodium cocylisethionate, cocoamide monoethanolamine) and fibers, fines, and/or filaments (e.g., cellulose fibers) may be combined in an amalgamator. In some examples, antimicrobial agents (e.g., zinc pyrithione) and/or fragrances may also be combined in the amalgamator. The surfactant/preservative solution may then be added into the amalgamator and the composition may be mixed until visually homogeneous. In one example, formation of the cleansing composition may occur at room temperature. Suitable examples of surfactants; fibers, fines, and/or filaments; and other ingredients are described hereinbelow and in U.S. Patent Publication Nos. 2015/0000057, 2015/0000058, 2015/0005223, all published on Jan. 1, 2015.

In certain examples, the cleansing composition (e.g., cleansing composition puck 36) may be compliant. For example, a cleansing composition may exhibit an acceptable level of compliance of from about 0.01 kg/mm to about 1.5 kg/mm, as measured by the Compliance Test described hereinbelow. In certain examples, a cleansing composition may exhibit compliance values of from about 0.03 kg/mm to about 1.0 kg/mm; about 0.10 kg/mm to about 0.75 mm/kg; about 0.10 kg/mm to about 0.6 kg/mm; about 0.05 kg/mm to about 0.5 kg/mm; or about 0.10 kg/mm to about 0.30 kg/mm.

Upon formation, a loosely-amalgamated cleansing composition may be transferred to a plodder or other mixing equipment and subsequently plodded or otherwise mixed. In one example, prior to plodding, the loosely-amalgamated cleansing composition may be transferred from the amalgamator to a conventional roll mill and passed through one or more times. In one example, the loosely-amalgamated cleansing composition may be placed in drums for transport and/or storage prior to plodding. In certain examples, a plodded extrudate cleansing composition may be unitized by a wire cutting tool to form, for example, a cleansing composition puck 36, as shown in FIG. 6. However, it will be appreciated that a cleansing composition may be provided in any of a variety of suitable shapes and configurations and may be unitized by any of a variety of other methods such as, for example, rotary molding or substituting a blade for the wire cutting tool. Accordingly, the method of making a personal care article may further include forming a loosely-amalgamated cleansing composition, plodding the loosely-amalgamated cleansing composition, and unitizing a plodded extrudate cleansing composition to form a cleansing composition puck 36.

Figure 7:
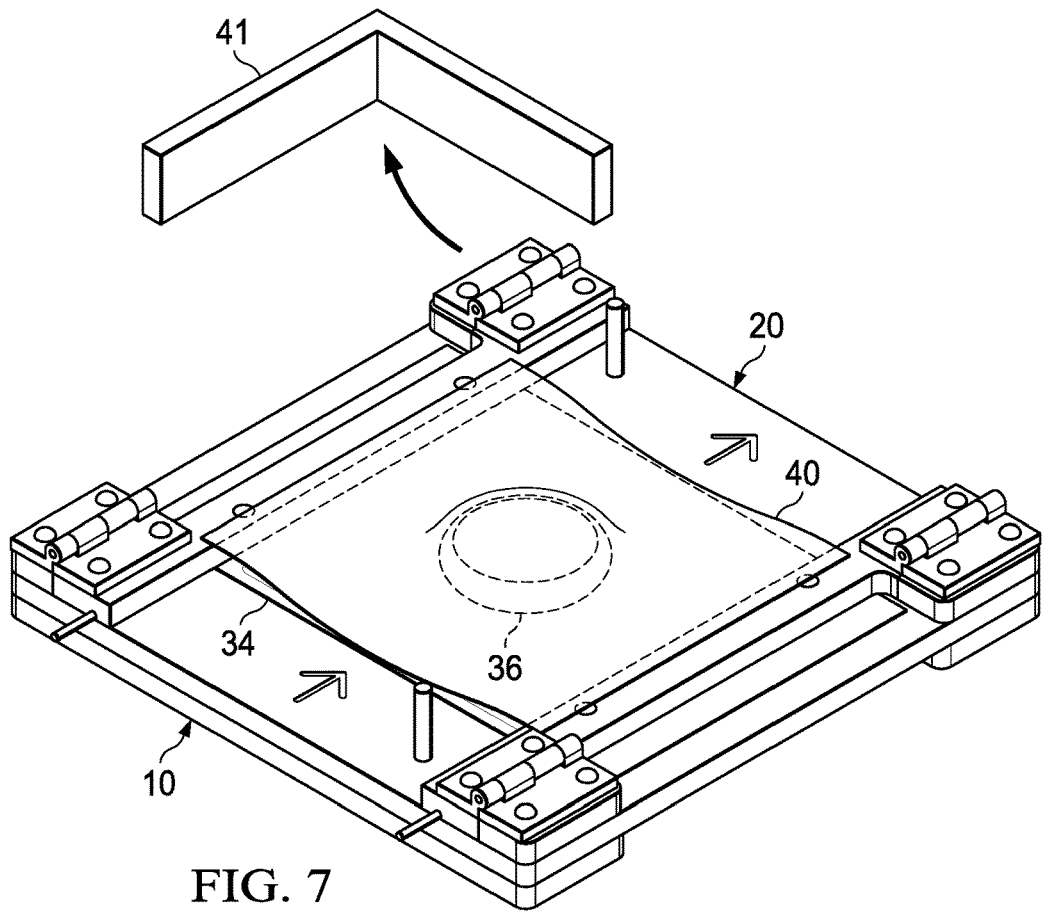
FIG. 7 depicts an isometric view of the converting frame, the anvil plate assembly, the lower film, and the cleansing composition puck of FIG. 6, with an upper film placed over the cleansing composition puck and the lower film and where the first and second clamping wings remain in a closed position.

The method of making a personal care article may further include positioning at least one upper substrate (e.g., 40) over the cleansing composition (e.g., 36) and the at least one lower substrate (e.g., 34). In certain examples, and as shown in FIG. 7, an upper film 40 may be placed over the cleansing composition puck 36 and the lower film 34. The upper film 40 may completely cover the cleansing composition (e.g., 36), as shown, for example, in FIG. 7, and in certain examples, the upper film 40 may also substantially cover and/or substantially be aligned with the lower film 34. In certain examples, the at least one upper substrate (e.g., 40) may be loosely laid over the cleansing composition (e.g., 36), such that the at least one upper substrate (e.g., 40) is not secured within the converting frame 20.

The lower film 34 and the upper film 40 are shown in FIGS. 4-7 to be substantially rectangular; however, it will be appreciated that lower substrates and upper substrates may be provided in any of a variety of shapes and sizes. In one example, the at least one lower substrate (e.g., 34) and the at least one upper substrate (e.g., 40) may be provided as square-shaped with sides of about 7 inches. Further, while one upper film 40 is shown in FIG. 7, it will be appreciated that in other examples, two or more upper substrates may be laid over a cleansing composition and/or the one or more lower substrates (e.g., 34). In one example, the at least one upper substrate may include two upper films, where a first upper film may be formed of polypropylene and polyethylene and a second upper film may be formed of polyethylene. When assembled, the first upper film may be positioned over the second upper film, such that the first upper film may be an outermost layer of the personal care article and the second upper film may separate the first upper film from the cleansing composition. In such an example, polypropylene fibers of the first upper film comprise an outer surface of the first upper film. As described above, other suitable examples of substrates and films are described herein below and in U.S. Patent Publication Nos. 2015/0000057, 2015/0000058, 2015/0005223, all published on Jan. 1, 2015.

The method of making a personal care article may further include placing the converting frame 20 and the anvil plate assembly 10 on a target location of a heat press (not shown). In certain examples, a first physical guide (e.g., 41) may facilitate positioning of the converting frame 20 and anvil plate assembly 10 on the target locations of the heat press. As shown in FIG. 7, the first physical guide can be one or more rails 41 (e.g., a side rail and a back rail, aligned perpendicularly to provide a corner). However, it will be appreciated that a first physical guide can be provided in any of a variety of other suitable configurations. The method of making a personal care article may further include actuating the heat press to direct a heated seal plate 42 onto the anvil plate 12, thereby contacting the at least one upper substrate (e.g., 40) to form a seal 44 between the at least one upper substrate (e.g., 40) and the at least one lower substrate (e.g., 34) and thereby contain the cleansing composition (e.g., 36) between the at least one upper and lower substrates.

In one example, the at least one upper substrate may include a first upper film that is an outermost layer of the personal care article and formed of polypropylene and polyethylene and a second upper film formed of polyethylene, and the at least one lower film may include a first lower film may be formed of polyethylene and a second lower film that is an outermost layer of the personal care article and may include a textured surface (e.g., textured surface for scrubbing). In such an example, the seal plate 42 may be heated such that upon contact with polypropylene fibers on an outer surface of the first upper film, the polyethylene of the upper and lower films may melt and bond to each other without adhering to the seal plate 42. In one example, the seal plate 42 may be heated to a temperature of from about 250° F. to about 300° F.; about 260° F. to about 290° F.; about 265° F. to about 280° F., or about 270° F. However, it will be appreciated that a seal plate may be heated to any temperature suitable to effect a sufficient seal for a personal care article.

Figure 8:
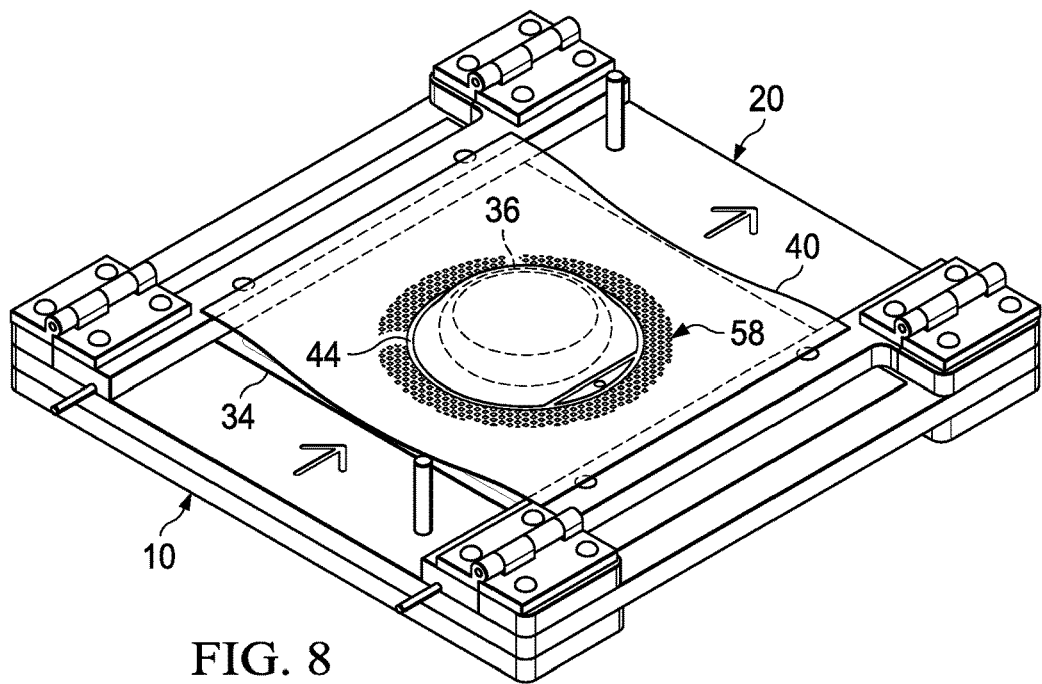
FIG. 8 depicts an isometric view of the converting frame, the anvil plate assembly, the lower film, the cleansing composition puck, and the upper film of FIG. 7, with a seal between the upper film and the lower film.
Figure 9:
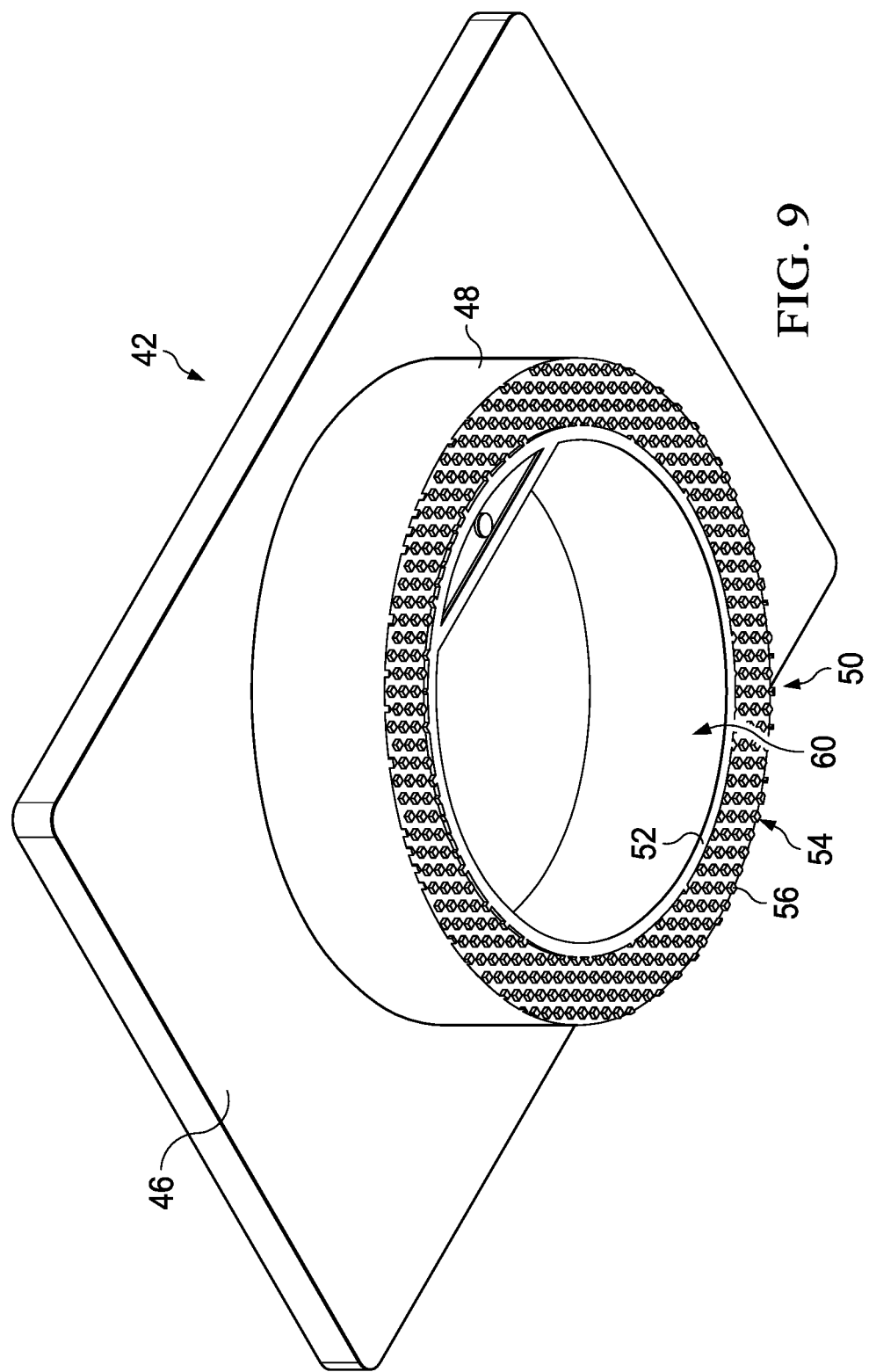
FIG. 9 depicts an isometric view of a bottom side of a seal plate used to form the seal depicted in FIG. 8.

FIG. 8 depicts the cleansing composition (e.g., 36) contained between the at least one upper substrate (e.g., 40) and the at least one lower substrate (e.g., 34) by the seal 44, which has been formed by the heat press. As described above, the heat press may include the seal plate 42, as shown in FIG. 9, which may be heated and placed in contact with the at least one upper substrate (e.g., 40). In certain examples, the seal plate 42 is formed of aluminum. However, it will be appreciated that a seal plate may be formed of any of a variety of suitable materials.

In certain examples, the seal plate 42 may include a base plate 46, a wall 48 extending perpendicularly from the base plate 46, and a substrate-contacting portion 50 on a surface of the wall opposite to and substantially in parallel with base plate 46. As shown in FIG. 9, the substrate-contacting portion 50 may include a substantially flat and continuous inner perimeter 52, and an outer perimeter 54, where the outer perimeter 54 may include a plurality of knurls 56. In one example, the substantially flat and continuous inner perimeter 52 may contact the at least one upper substrate (e.g., 40) to form the seal 44, and the outer perimeter 54, including the plurality of knurls 56, may contact the at least one upper substrate (e.g., 40) to form a knurl bond 58. As shown, for example, in FIG. 8, the knurl bond 58 may be formed outwardly adjacent to the seal 44. In some examples, it is believed that the seal 44 may assist in preventing bulk loss of cleansing composition (e.g., 36) from the personal care article and may provide sufficient seal strength for maintaining the integrity of the personal care article throughout consumer use. In some examples, the knurl bond 58 may provide a high quality finished appearance that is consumer-preferred while eliminating formation of a thin, hard surface on a periphery of the personal care article. However, while the substrate-contacting portion 50 of FIG. 9 is shown to include the outer perimeter 54 including the plurality of knurls 56, it will be appreciated that in other examples, a seal plate may be free of knurls such that a personal care article may not include a knurl bond.

In one example, the inner perimeter 52 may be about 3 mm wide and the outer perimeter may be about 10 mm wide. In one example, each of the plurality of knurls 56 may exhibit a surface area of about 1 mm by 1 mm. In one example, the inner perimeter 52 and one or more of the plurality of knurls 56 of the substrate-contacting portion 50 may have a height of about 1 mm. It will be appreciated, however, that a substrate-contacting portion may have any of a variety of suitable dimensions. While the inner perimeter 52 and the outer perimeter 54 of the substrate-contacting portion 50 are shown in FIG. 9 to be circular, it will be appreciated that the substrate-contacting portion 50 may be any of a variety of suitable configurations or shapes such as, for example, hexagonal. In certain examples, the base plate 46 and the wall 48 may define a seal plate cavity 60. In one such example, a depth of the seal plate cavity 60 may be about 1.5 inches (38.10 mm). A thickness of a personal care article may be less than the depth of the seal plate cavity 60.

Figure 10:
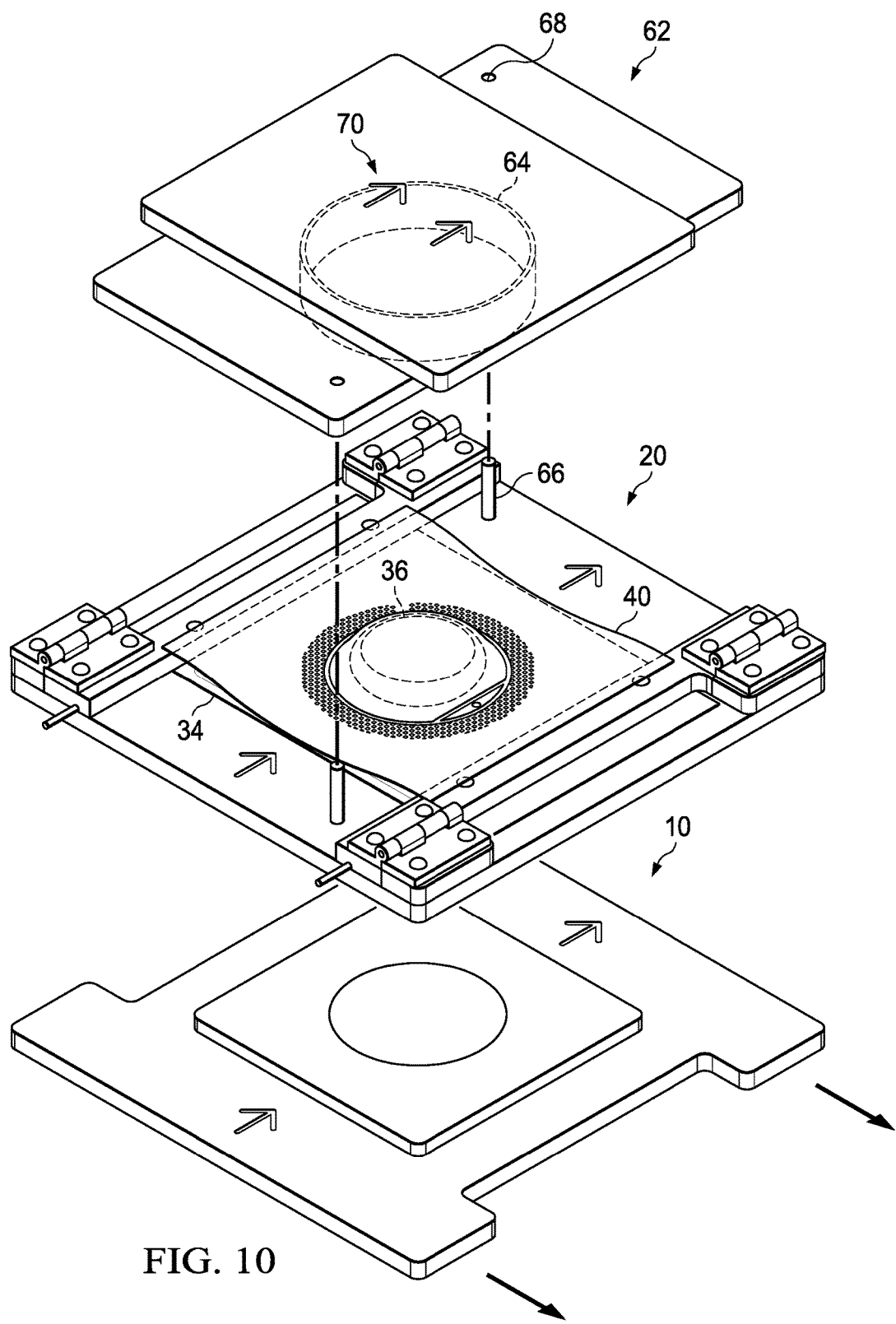
FIG. 10 depicts an isometric, exploded view of a die assembly over the converting frame over the anvil plate assembly, where the lower film, sealed to the upper film, remains secured within the converting frame as in FIG. 8.

In certain examples, the method of making a personal care article may further include separating the anvil plate assembly 10 from the converting frame 20, as shown in FIG. 10. Upon separation from the anvil plate assembly 10, the lower film 34, supporting the cleansing composition puck 36 and sealed to the upper film 40, remains secured within the converting frame 20. In certain examples, the method of making a personal care article may further include placing the converting frame 20 on a surface of a cutting press (not shown).

Figure 11:
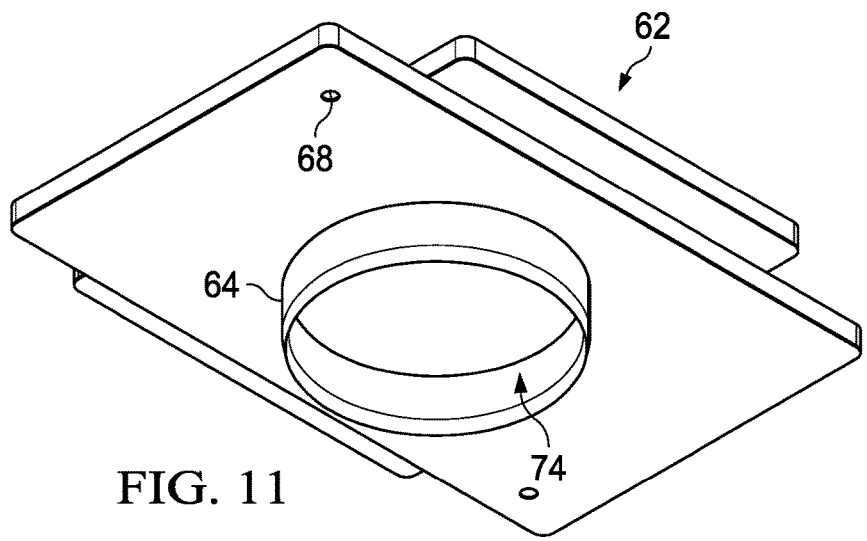
FIG. 11 depicts an isometric view of a die on bottom side of the die assembly of FIG. 10.
Figure 12:
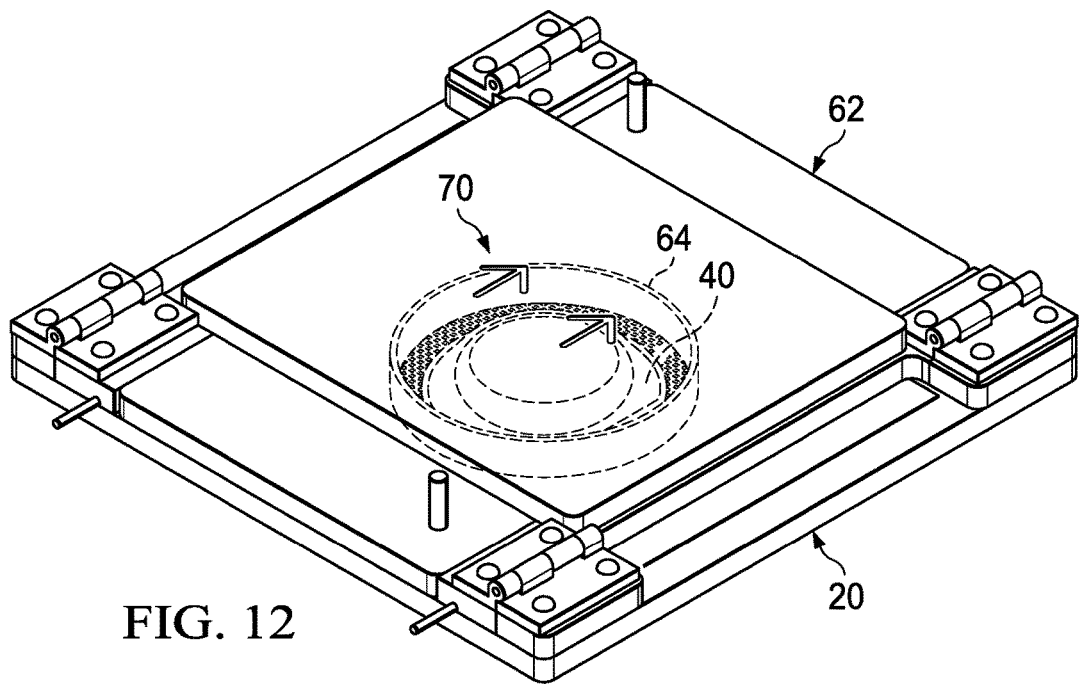
FIG. 12 depicts an isometric view of the die assembly and the converting frame of FIG. 10, where the die of FIG. 11 is in contact with the upper film.

The method of making a personal care article may further include placing a die assembly 62 comprising a die 64, as shown in FIG. 11, over the at least one upper substrate (e.g., 40) on the converting frame 20, such that the die 64 is facing the surface of the cutting press, as shown in FIGS. 10 and 12. The converting frame 20 may further include one or more physical guides (e.g., 66) for facilitating placement of the die assembly 62 on the converting frame 20. As shown in FIGS. 10 and 11, the die assembly 62 may define apertures 68, which may be configured to receive guide posts 66 on the converting frame 20. In certain examples, the apertures 68 and the guide posts 66 may be substantially similarly sized such that, when the die assembly 62 and the converting frame 20 are in contact with each other (e.g., assembled together), the apertures 68 may receive the guide posts 66 to provide a fit that can minimize relative movement between the die assembly 62 and the converting frame 20, yet not hinder an operator's ability to separate the die assembly 62 and the converting frame 20 when desired.

Like the anvil plate assembly 10 and the converting frame 20, the die assembly 62 may further include one or more indicators to facilitate identification of a preferred orientation. As shown in FIGS. 10 and 12, the die assembly 62 may include a third set of arrows 70. And like the converting frame 20 and the anvil plate assembly 10, the die assembly 62 may be substantially transparent, such that an operator may be able to verify the desired alignment of the die assembly 62 over the converting frame 20 while the die assembly 62 and the converting frame 20 are in contact with each other (e.g., assembled together as shown in FIG. 12). Further, while the die 64 is shown in FIGS. 10-12 to be circular, it will be appreciated that a die may be any of a variety of suitable configurations or shapes such as, for example, hexagonal.

Figure 13:
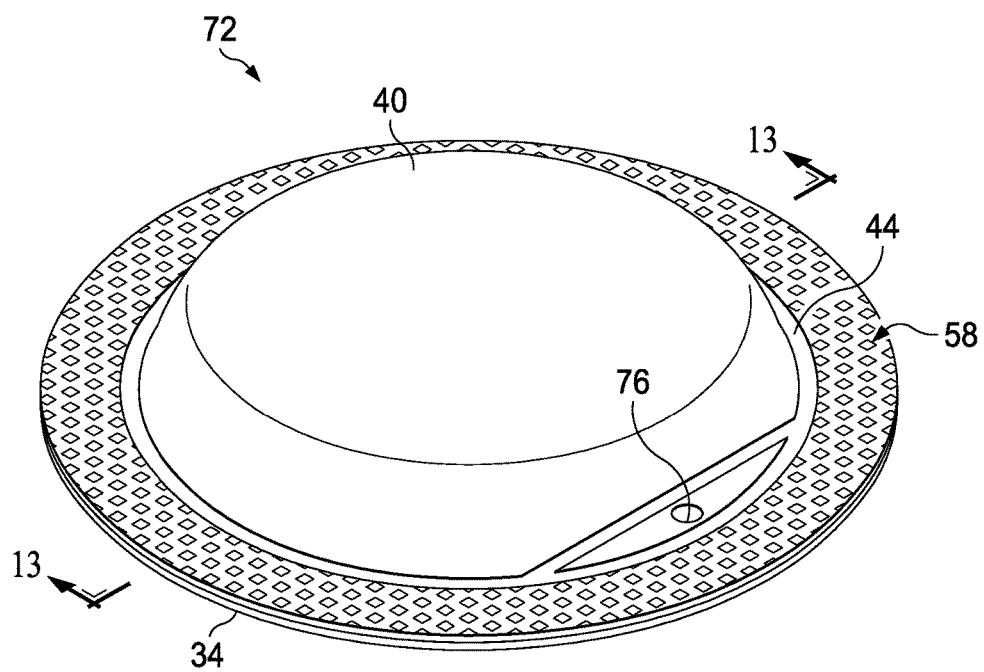
FIG. 13 depicts an isometric view of a personal care article, according to one example.
Figure 14:
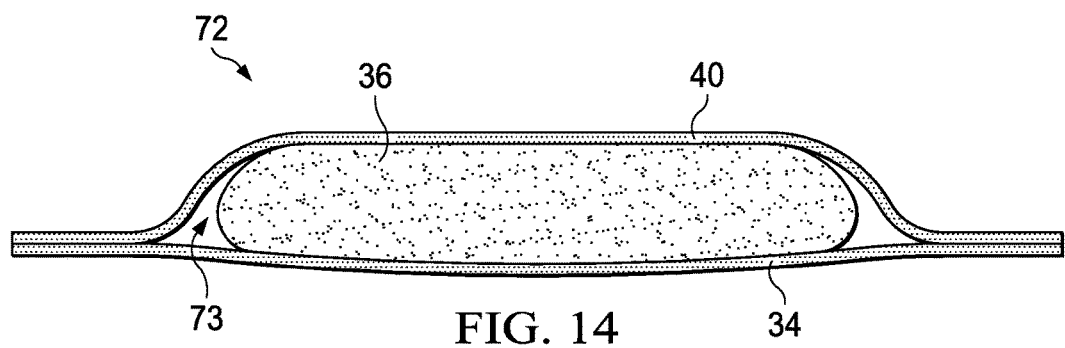
FIG. 14 depicts a cross-sectional view of the personal care article of FIG. 13, along line 13-13.

In certain examples, the method of making a personal care article may further include actuating the cutting press to drive the die assembly 62 onto the converting frame 20 to cut excess portions of the at least one lower substrate (e.g., 34) and the at least one upper substrate (e.g., 40) at or outwardly adjacent to the seal 44 to form the personal care article 72, which is shown in FIGS. 13 and 14. In certain examples, actuating the cutting press to drive the die assembly 62 onto the converting frame 20 may include cutting the excess portions of the at least one lower substrate (e.g., 34) and the at least one upper substrate (e.g., 40) at or outwardly adjacent to the knurl bond 58, as shown, for example, in FIG. 13. It is believed that cutting the excess portions at the knurl bond 58 may reduce the risk of inadvertently cutting the seal 44 and creating an opening for bulk loss of cleansing composition (e.g., 36) from the personal care article 72.

In certain examples, actuating the cutting press to drive the die assembly 62 onto the converting frame 20 may further include shaping the cleansing composition (e.g., 36). In such examples, shaping the cleansing composition (e.g., 36) may include compressing the cleansing composition (e.g., 36) with the die assembly 64. As shown, for example, in FIG. 14, the personal care article 72 may further include a chamber 73, an open area between the at least one lower substrate (e.g., 34) and the at least one upper substrate (e.g., 40) in which the cleansing composition (e.g., 36) may be contained. As shown in FIG. 11, the die 64, along with the die assembly 62, may define a die cavity 74. In certain embodiments, a depth of the die cavity 74 may be less than a height of the cleansing composition (e.g., 36) prior to actuation of the cutting press, such that when the die assembly 64 is driven onto the converting frame 20 to cut excess portions of the at least one lower substrate (e.g., 34) and the at least one upper substrate (e.g., 40), a surface of the die assembly 62 within the die cavity 74 may contact the at least one upper substrate (e.g., 40) to shape or compress the cleansing composition (e.g., 36) into outer portions of the chamber 73. In such embodiments, the cleansing composition (e.g., 36) may be shaped to at least partially conform to a shape defined by the die cavity 74. In some embodiments, sidewalls of the die cavity 74 may contact the at least one upper substrate (e.g., 40) to shape the cleansing composition (e.g., 36). It is believed that providing for final shaping of the cleansing composition (e.g., 36) at this stage in the method of making a personal care article (i.e., by the die assembly 64) may enable a preferred aesthetic while minimizing the risk of waste at a prior stage of the method. For example, allowing for shaping or compression of a cleansing composition (e.g., 36) by a heated seal press could cause contamination in a resulting seal.

In one example, the method of making a personal care article may further include creating a hanger hole 76 adjacent to or within the seal 44 and feeding a hanger (not shown) therethrough. Suitable hangers may include chords, hooks, loops, twines, strings, elastic bands, etc. and may include synthetic and/or natural materials including fibers, and may be molded, such as injection molded. In certain examples, the hanger may include a single piece or multiple pieces fastened together. In one example, the multiple pieces may include corresponding male and female elements and the fastening mechanisms may include, for example, snaps, buttons, hook and eye, etc. In one example, the method of making a personal care article may further include providing a vapor barrier (not shown) for the personal care article 72 and sealing the personal care article 72 therein.

Personal Care Articles

A personal care article comprises a substrate (e.g., film) and a personal care composition (e.g., cleansing composition). In certain examples, the personal care article may include from about 40% to about 99.6%, by weight of the article, of a cleansing composition. Additional acceptable ranges of cleansing composition may include from about 50% to about 99% or from about 75% to about 98%, by weight of the article. In certain examples, one or more substrates may fully or at least partially surround the cleansing composition. The one or more substrates may be adjacent to the cleansing composition, another substrate, or a combination thereof. A personal care article may comprise a contact substrate, non-contact substrate, or combinations thereof. Contact substrates are those on the exterior of the article likely to make direct contact with the target surface, while non-contact substrates are those not likely to make contact with the target surface. A personal care article may be used, for example, on skin, hair, or both. A personal care article may also be used, for example, for cleansing of the skin, cleansing of the hair, shave preparation, post shave treatment, or a combination thereof. A personal care article may be a personal cleansing article. A personal care article may also be reusable.

Adding a substrate to a cleansing composition may present its own challenges. For example, a substrate may change an amount of water available to the cleansing composition at the outset which may impact lather, rate of consumption, and surfactant release. The substrate may also change the dynamics with the cleansing composition during use. For example, the substrate may retain water in close proximity to the cleansing composition. It may also impact the cleansing composition after use by, for example, limiting the exposure of the cleansing composition to the air to inhibit drying after use. All of these factors may be considered when creating a personal care article and the properties of the cleansing composition and the article are balanced so that the article has the desired characteristics. This is especially true where the cleansing composition and/or article are to be compliant throughout the lifetime of the article.

A personal care article may also be compliant. For example, if the article is a personal care article for cleansing the skin, then the article will bend to some degree to more fully contact a curved body part like the arm. Thus, if the personal care article is originally flat with no curve, when applied to the arm for cleansing there would be some amount of bend to better conform to the arm. Oppositely, if the original article is curved such that it would not need to bend to conform to a curved surface like the arm, then it would bend to straighten when applied to a less curved surface like the abdomen. A personal care article may be fully compliant meaning it is capable of completely conforming to the surface to which it is applied.

Compliance of a personal care article may be measured according to the Compliance Test described in more detail below. As described above with respect to the cleansing composition, the personal care article may exhibit a compliance value of about 1.50 kg/mm or less, as measured by the Compliance Test described herein below. Additional examples of suitable compliance values include from about 0.01 kg/mm to about 1.5 kg/mm; from about 0.03 kg/mm to about 1.0 kg/mm; about 0.10 kg/mm to about 0.75 mm/kg; about 0.10 kg/mm to about 0.6 kg/mm; about 0.05 kg/mm to about 0.5 kg/mm; or about 0.1 kg/mm to about 0.3 kg/mm.

In certain examples, the article and/or cleansing composition may become compliant after exposure to water. Thus, a non-compliant article or cleansing composition may, after exposure to a liquid, like water, during use, become compliant. If an article or cleansing composition becomes compliant by the end of a second simulated use, then it is considered compliant.

The personal care article may include from about 0.5% to about 25,000%, by weight of total substrate(s), of a cleansing composition. In one example, the article comprises greater than 3,500%, by weight of the total substrate(s), of a cleansing composition. In other examples, the article comprises greater than 4,000%, by weight of the total substrate(s), of a cleansing composition; greater than 4,250%, by weight of the total substrate(s), of a cleansing composition; greater than 4,500%, by weight of the total substrate(s), of a cleansing composition; greater than 4,750%, by weight of the total substrate(s), of a cleansing composition; greater than 5,000%, by weight of the total substrate(s), of a cleansing composition; or any combination thereof.

The personal care article may be in any suitable regular or irregular shape, for example, oval, square, rectangular, circular, triangular, hour glass, hexagonal, c-shaped, etc. Furthermore, the article may be sized based upon the desired use and characteristics of the article. An article may range in surface area size, for example, from about a square inch to about hundreds of square inches. An article may also have a surface area of, for example, about 5 in$^2$ (3,225.8 mm$^2$) to about 200 in$^2$ (129,032 mm$^2$), from about 6 in$^2$ (3,871.0 mm$^2$) to about 120 in$^2$ (77,419.2 mm$^2$), or from about 15 in$^2$ (9,677.4 mm$^2$) to about 100 in$^2$ (64,516 mm$^2$). An article may also have a certain thickness, for example, of from about 0.5 mm to about 50 mm, from about 1 mm to about 25 mm, or preferably from about 2 mm to about 20 mm. There may also be multiple compositions within zones in the article. These are described more fully in U.S. Pat. App. Pub. Nos. 2013/0043145, 2013/0043146, and 2013/0043147.

The cleansing composition may have a consumption, for example, of about 0.5 g to about 14 g per use; about 0.5 g to about 8 g per use; about 0.5 g to about 7 g per use; or about 0.5 g to about 6 g per use, as measured by the Consumption Test.

A substrate may also comprise a feature. Substrate features may include, for example, design elements such as shapes and letters. Substrate features may reside, for example, within land portions, surface aberrations, or a combination thereof and may be located in plane, above plane, or below plane, or combinations thereof relative to either the land portion or surface aberration. Substrates with features out of plane with both the land and surface aberration portions are considered multiplanar substrates.

The personal care article may also further include a use indicator, which may assist in signifying to a user when the personal care article has reached or is reaching the end of its useful life. In certain examples, a use indicator may take the form of, for example, a strip which changes color as the article is used. Additional examples of use indicators may include printed inks, dyes, pigments, slot or spray coated polymers containing, for example, inks, dyes or pigments.

Substrates

A personal care article may include at least one substrate (e.g., film), as described above. The substrate may enhance cleansing and therapeutic treatment of a surface such as skin and/or hair. For example, by physically coming into contact with the skin and/or hair, the substrate may aid in the cleansing and removal of dirt, makeup, dead skin, and other debris such that the substrate may act as an efficient lathering and/or exfoliating implement but may also be non-abrasive to the skin. A substrate may be a composite (i.e., there are multiple plies to the substrate which may be of the same or different materials). In one example, the substrate may be water insoluble. In other examples, the substrate may be water penetrable. However, the personal care article may comprise both water penetrable substrates and water insoluble substrates.

Substrates may be arranged in many different configurations on an article. Some examples of these configurations may be found, for example, in U.S. Pat. No. 6,491,928; U.S. Pat. App. Pub. Nos. 2013/0043146; 2012/0246851; 2013/0043145; and 2013/0043147, each of which is incorporated herein by reference. In certain examples, and as described above, substrates may fully or at least partially surround a cleansing composition. Substrates may also fully or at least partially surround or be adjacent to other substrates. The at least one lower substrate (e.g., 34) and the at least one upper substrate (e.g., 40), as described above, may be flexible such that they touch the cleansing composition (e.g., 36) or another substrate in some areas and not others. The areas where the substrate is touching or not touching the cleansing composition or other substrate may shift as the substrate(s) and composition shift during handling and/or use.

The substrate may be, for example, a formed film, like a vacuum formed film. The substrate could be a nonwoven (i.e., a natural or synthetic nonwoven including fibrous and nonfibrous nonwovens), which may typically have land regions (i.e., regions that do not allow water and/or cleansing composition to pass through) and openings; a woven; a film (e.g., a formed film); a sponge, which may include a natural and/or synthetic sponge (e.g., polymeric mesh sponge), examples of which may include those described in European Patent Application No. EP 702550 A1 published Mar. 27, 1996; a polymeric netted mesh (i.e., a "scrim"), examples of which may include those described in U.S. Pat. No. 4,636,419, each of which is incorporated herein by reference; a batting; spunbond; spunlace; hydroentangled; carded; needlepunch; or any other suitable material. In certain examples, the substrate may be a composite material that may include, for example, one or more plies of the same or different materials such as nonwovens, wovens, films, sponges, scrims, battings, and the like superimposed physically, joined together continuously (e.g., laminated, etc.) in a discontinuous pattern, or by bonding at the external edges (or periphery) of the substrate and/or at discrete loci. Suitable examples for each type of substrate and other suitable substrate materials are described in U.S. Pat. App. Pub. No. 2012/0246851, which is incorporated herein by reference.

Parameters to consider when selecting substrates (e.g., formed films) may include thickness, pattern, polymer stiffness, and permeability. Additional information on such parameters is also described in U.S. Pat. App. Pub. No. 2012/0246851, which is incorporated herein by reference.

A substrate may include one or more openings such that water, the cleansing composition, and/or lather, for example, may pass through the substrate. In one example, where a permeable substrate may be adjacent to the cleansing composition, water may pass through the water permeable substrate to interact with the cleansing composition. As the cleansing composition dissolves, it may then also pass through the substrate to be delivered to a target surface (e.g., skin).

In one example, permeability of openings may be selected based on a dissolution half-life of a cleansing composition and a desired reusability of the article. For example, when the dissolution half-life of the cleansing composition is high, a higher level of permeability may be selected to counteract the high dissolution half-life and provide a desirable consumption rate for the article. Alternatively, when the dissolution half-life of the cleansing composition is low, the permeability of the one or more openings or may be lower and still provide a desirable consumption rate for the article. A substrate may include, for example, a permeability of about 1 opening/cm$^2$ or greater, about 10 openings/cm$^2$ or greater, about 100 openings/cm$^2$ or greater, about 500 openings/cm$^2$ or greater, about 1,000 openings/cm$^2$ or greater, about 1,500 openings/cm$^2$ or greater, or any combination thereof.

The openings may be apertures. For example, the one or more openings may include well-defined apertures such as microapertures or macroapertures, holes, perforations, cavities, raised or depressed fibrous and/or nonfibrous regions, gaps between regions, and the like that may enable, for example, water and/or the cleansing composition to pass through the substrate.

A substrate may be a contact substrate, which may be a substrate for contacting a target surface (e.g., skin). A substrate may also be a noncontact substrate. Noncontact substrates, for example, may be used to help give a personal care article a desired consumption rate, softness, lather properties, strength, etc.

Substrates may further include a surface aberration, such as a raised portion on a surface of a substrate. It may be readily apparent to the naked eye and may form a geometric pattern on a substrate. In one example, the geometric pattern does not require registration on the assembled article. In certain examples, surface aberrations may be from about 700 μm to about 7000 μm in height (the z-direction). Surface aberrations may also be macroapertured. In certain examples, the surface aberrations may provide thickness without itself being a single pore, while the conventional portions of the substrate may provide a larger number of pores to promote lather generation. Particularly, multiplanar substrates with a thickness from about 700 μm to about 7000 μm may allow for enough water, surfactant, and air to pass through such that the sufficient lather may be generated.

Surface aberrations may also provide an exfoliation benefit. In order to provide exfoliation with a monoplanar film, pores with a large diameter may be required in order to achieve a significant z-dimension. This concentrates the applied force over a smaller contact area with the skin, making the substrate feel scratchy. Conversely, multiplanar films may include surface aberrations with larger z-dimensions. Such surface aberrations may contribute to the exfoliating properties of the film and more directly control the surface area over which an applied force is distributed, thereby reducing a scratchy perception of the substrate. Additionally, by incorporating a minimum number of pores per square inch, about 10 (local), the issue with a scratchy feel related to pore size may also be abated.

Land area of a substrate may impact consumer acceptance of the product. For example, consumers may view films with larger amounts (e.g. about 55% or more) of land area as looking too much like plastic. In order to combat this consumer perception, a substrate may include more surface aberration area (e.g. about 45% or more).

Substrates may include about 45%, about 50%, about 55%, about 60%, about 65%, about 70%, about 75%, to about 50%, about 55%, about 60%, about 65%, about 70%, about 75%, about 80%, about 85%, about 90%, about 95%, about 98%, or any combination thereof, of surface aberration area. The amount of surface aberration area and land area may be determined by measuring the dimensions geometrically in the x-y (flat planar) direction for the unit cell of the substrates for their planar projection, for example, with a ruler or a caliper. It may be convenient to use a magnifying technique to measure fine dimensions. Surface aberration and land area may be estimated from geometries of processing equipment used to make the structures, which are usually known from design, although these are only estimates since substrates may shrink or stretch during subsequent processing. Thus, land area and surface aberration area may be expressed as a percentage of land (or surface aberration) area within a unit cell divided by the total area of the unit cell. Where the pattern on the substrate is irregular such that no unit cell exists, the percentage of land or surface aberration area is expressed as the amount of land (or surface aberration) area of the article surface utilizing the substrate pattern in question divided by the total area of the article surface utilizing the substrate pattern in question. A surface aberration may be part of a unit cell which is generally the smallest repeating unit (other than pores, if applicable). The calculation is determined with the substrate oriented such that the protuberances or pores are in the upward direction, pointing normal to the viewing plane. For instance a circular aberration motif with a diameter of 0.25 mm and a unit cell area of 0.625 mm$^2$ would have a percentage surface area of aberration of approximately 7.85%.

Too much surface aberration area may impact the integrity of a substrate and may, for example, lower the resistance of the substrate to tearing. Thus, the amount of surface aberration area may be balanced among scratchiness, consumer acceptable look, and longevity based on the desired properties of the substrate.

Surface aberrations may be permanent deformations in a substrate, such that after they are formed, no force is required to maintain the raised or depressed state. Surface aberrations may be formed through a process, like, vacuum forming, for example. So, actions like cinching and gathering do not generally form surface aberrations, but puckers in a substrate. These surface aberrations may also contain pores. To form a plane, as discussed below, at least some of the surface aberrations will contain at least three protuberances that are not in a row. A surface aberration may have up to about 250,000 protuberances on its surface. A surface aberration may form a pattern or design. Surface aberrations may have an area of, for example, about 0.005 cm$^2$ or more, about 0.01 cm$^2$ or more, or about 0.07 or more.

Surface aberrations may include edges connecting their surface to a base substrate. These edges are formed during processing of the substrate to make the surface aberrations. During processes like vacuum forming, these edges maintain a similar thickness to that of the substrate before processing. This may help with stability of the substrate when it is processed into rolls. Some processes, like those used to form embossments and debossments, stretch the substrate resulting in edges to the embossments and debossments that are thinner than that of the substrate before processing which may cause issues with stability of the substrate when processing into rolls for transport.

Surface roughness may be added in the land area, in the portion of surface aberration areas that are closed, and/or on features, of substrates. Creating surface roughness may result in a reduction of the gloss of the substrate surface which corresponds to a preferred consumer appearance. Gloss values may be, for example, less than about 3.5 or less than about 2.5.

A substrate may be multiplanar. For example, a first plane may be defined by land area on the surface aberrations and a second plane may be defined by the land area of the base film. The second plane may be, for example, contiguous and repeating and generally non-porous. The second plane may generally be flat or may be flattened merely by placing the substrate on a table. The transition from the first plane to the second plane may be discrete or the transition may be stepped, tapered, or occur at an angle less than about 90 degrees but greater than 0 degrees. The first plane may be, for example, discontinuous. The first plane may be flat, raised, or even curved, so that it is not planar in the formal geometric sense, and is used to describe a base region from which protrusions may be raised and generally extends in an orthogonal direction to the protrusions and is the same plane as the original film from which the protrusions were raised. Surface aberrations which are similar (in the geometric sense) may be considered to be in the same plane even if they are not connected to one another. Where the surface aberrations are dissimilar (for example, different heights from the plane of the original film), then they may create multiple planes.

Features, which may be continuous or discrete, may be added to the substrate and may represent additional planes or even add texture, for example patterns like starts, squares, logos may be embossed onto the substrate. Features may also be at the same level of an existing plane, and may be considered part of an existing plane, and not an additional plane. For example, a formed film may be considered a planar substrate. A seal on a substrate is usually on such a similar level to an existing plane that it is considered as part of the existing plane and not creating an additional plane.

Some examples of suitable substrates are included below.

| 1. Formed Films | | | |
|---|---|---|---|
| Code | Material Description | Caliper and Basis Weight | Pore count/ area; and diameter |
| F1 | Hydroapertured polyethylene film on 100 mesh screen, white (Tredegar, Inc.) | 166 microns, 24.5 gsm | 1,780/cm$^2$ — |
| F2 | Vacuum formed polyethylene film, white (SSRIS-CPM, Tredegar, Inc.) | 560 microns, 24.5 gsm | 115/cm$^2$ |
| F3 | Vacuum formed polyethylene film, white 22 Hex (Tredegar, Inc.) | 560 microns, 24.4 gsm | 91/cm$^2$ ~500 micron |
| F4 | Vacuum formed polyethylene film, blue 11.2 Hex (Tredegar, Inc.) | 935 microns, 29.4 gsm | 22.2/cm$^2$ 1.1 mm |
| F5 | Vacuum formed polyethylene film, green (Tredegar, Inc.) | 670 microns, 36.0 gsm | 49/cm$^2$ 0.9 mm |
| F6 | Vacuum formed polyethylene film, white (Tredegar, Inc.) | 33.5 gsm | 12.6/cm$^2$ 1 mm |
| F7 | Vacuum formed polyethylene film 40 Hex | 418 microns, 35.8 gsm | 285/cm$^2$ — |
| F8 | Vacuum formed polyethylene film 8.75 Hex | 950 microns, 37.4 gsm | |

Caliper: ASTM D645
Air Permeability: ASTM D737

| 2. Fibrous Nonwovens | | |
|---|---|---|
| Code | Material Description | Basis Weight |
| N1 | Spunlaid hydroentangled 100% PP (Avgol Nonwovens, NC, USA) | 47 gsm |
| N2 | Carded, calendar bonded all bicomponent PP/PE fiber (Fiberweb Inc., TN, USA) | 32 gsm |
| N3 | Spunbond, overbonded 100% PP (Experimental nonwoven) | 37 gsm |
| N4 | Carded, through air bonded 30/30/40 PP/Bicomponent PP-PE/Rayon (calendar patterned) | 62 gsm |

| 3. Fibrous Nonwoven Battings | | |
|---|---|---|
| Code | Material Description | Caliper; and Basis Weight |
| B1 | Quilter's Fusible batting, low loft all polyester (Fairfield Processing, Danbury, CT, USA) | 2.50 mm, 160 gsm |

-continued

3. Fibrous Nonwoven Battings

| Code | Material Description | Caliper; and Basis Weight |
|---|---|---|
| B2 | Quilter's Fusible batting, low loft all polyester, ½ thickness (peeled) | 1.21 mm, 80 gsm |
| B3 | PROEF 12-334 polyester-bicomponent fiber blend batting (Libeltex, Belgium) | 1.54 mm, 100 gsm |
| B4 | PROEF 12-370 dual layer PET/copet bico and PP fibers; bulk layer with standard PET/coPET bico trilobal fibers (Libeltex, Belgium) | 0.60 mm, 55 gsm |
| B5 | Dry Web T30 SC batting, hollow PET + bico PET/PE fiber blend, through air bonded (Libeltex, Belgium) | 0.41 mm, 35 gsm |
| B6 | PROEF 12-372 batting, coarse polyester and PE/PET bico fibers (Libeltex, Belgium) | 0.55 mm, 50 gsm |
| B7 | Dry Web T23W batting, coarse polyester and bico fiber mix (Libeltex, Belgium) | 0.56 mm, 50 gsm |

4. Laminate Films

| Code | Material Description | Basis Weight |
|---|---|---|
| L1 | Formed film nonwoven laminate | 34 gsm |

5. Multiplanar Films

| Example | pattern | design or post processing | Thickness (micron) | Number of Pores per Sq. In. |
|---|---|---|---|---|
| Multiplanar 1 | 30 hex | Multiplanar with star shape feature and hexagonal land area, land area 7% | 1724 | 1035 (local) |
| Multiplanar 2 | 30 hex | Multiplanar with circular raised areas further with letter 'O' feature | 2640 | 1035 (local) |
| Multiplanar 3 | 30 hex | Biplanar with hexagonal pattern | 2514 | 1035 (local) |
| Multiplanar 4 | 30 hex | Biplanar | 1597 | 1035 (local) |
| Multiplanar 5 | | Biplanar with circular raised areas and 30% HDPE resin, 0.025 in. plane height, gloss of 3.2 | 1985 | 1840 (local) |
| Multiplanar 6 | | Biplanar with circular raised areas and 30% HDPE resin, 0.040 in. plane height, gloss of 2.9 | 2080 | 1840 (local) |
| Multiplanar 7 | | Biplanar with circular raised areas, 30% HDPE resin, 0.055 in. plane height, gloss of 2.5 | 3550 | 1840 (local) |
| Multiplanar 8 | | Biplanar with circular raised areas, 30% land area | 2012 | 1840 (local) |
| Multiplanar 9 | | Biplanar with circular raised areas, 44% land area | 2421 | 1840 (local) |

Cleansing Compositions

In certain examples, and as described above, the cleansing composition (e.g., 36) may be compliant. In certain examples, the cleansing composition may maintain its compliance through the life of an article. For example, the cleansing composition or article may have an acceptable compliance, after 10 simulated uses, 12 simulated uses, 15 simulated uses, 20 simulated uses, 25 simulated uses, 30 simulated uses, or greater than 30 simulated uses. In one example, the cleansing composition or article may have a compliance value of 0.01 kg/mm to about 1.5 kg/mm after 12 hours of drying after 15 simulated uses. In another example, the cleansing composition or article may have a compliance value of about 0.10 kg/mm to about 0.75 kg/mm after drying for 12 hours after 10 simulated uses. Another factor to consider when developing an acceptable cleansing composition or article is its compliance after a long period of non-use. As such, it may be helpful to also look at whether a cleansing composition or article has an acceptable compliance level when measured 48 hours after the last use.

To solve such issues, in certain examples, the cleansing compositions may include hygroscopic filaments. Hygroscopic filaments may be made of fibers and fines. Without wishing to be limited by theory, it is believed the fibers and fines may work together to form a network. This is believed to be contributed to, in part, by the length and aspect ratio of the fibers. The ability to form a network may be an important feature in order to minimize the common tendency of materials to crack when they lose solvent (water drying). Solvent loss causes dimensional changes with materials due to the loss of solvent volume. The cleansing composition tends to therefore shrink, crack, or change its density. Shrinking and cracking are common in coatings when solvent is lost, the result of the internal stress created as the solvent volume is lost. It is more desirable for the cleansing composition to shrink (which is a flow, or it acts as a viscous material to relax the stress) instead of crack (which is an elastic behavior, not a flow). Cracking opens up fissures allowing even faster solvent loss throughout the cleansing composition. Without wishing to be limited by theory, it is believed the filament may not allow cracking to occur due to long range order, i.e., network behavior.

The aspect ratio of a fiber describes the relationship between the length and diameter of the fiber and may be calculated by dividing end to end length by diameter. Aspect ratios acceptable for fibers used herein may include those above about 9, above about 9.5, above about 10, above about 100, above about 1000, above about 10,000, to about 100, to about 500, to about 1000, to about 10,0000, to about 100,000, to about 300,000, or any combination thereof.

It is also believed that the hygroscopic water insoluble nature of filaments may further contribute to maintaining compliance upon repeated use. Hygroscopic filaments are water loving or hydrophilic by chemistry so may help to retain water in the cleansing composition. Additionally, by being water insoluble, certain filaments may remain in the cleansing composition even after exposure to water enabling them to continue contributing the properties of the composition through multiple uses instead of dissolving away. Other filaments may partially or fully dissolve during use enabling them to provide order to the composition and provide soluble components that may help plasticize the cleansing composition. It may be beneficial for filaments or portions of the filaments to exit an article during use. For example, filaments may exit the article through pores in the substrate and this may work to enhance scrubbing or to give the appearance the article is being depleted as the cleansing composition is used over time.

Another property that may have an impact on granular compositions is the angle of repose. The angle of repose is a measure of the flow ability of the particles in a granular composition and may impact processing of a granular composition. The angle of repose can be, for example, less than about 60° as measured by ASTM D6393.

Cleansing compositions may be in the form of a soft solid. Cleansing compositions may include a surfactant; and a hygroscopic fine, a hygroscopic fiber, or a combination thereof (i.e. a hygroscopic filament). The cleansing composition may include, for example, from about 1% to about 99.5%, or from about 10% to about 70%, or from about 20% to about 80%, or from about 20% to about 50%, by weight of the cleansing composition, of a surfactant or a mixture of surfactants. A surfactant may be, for example, in the form of a solid powder.

Suitable synthetic surfactants for a cleansing composition may include, for example, sulfates, sulfonates, alkyl sulfates, linear alkyl sulfates, branched alkyl sulfates, linear alkyl ether sulfates, branched alkyl ether sulfates, linear alkyl sulfonates, branched alkyl sulfonates, linear alkyl ether sulfonates, branched alkyl ether sulfonates, alkyl aromatic sulfates, alkyl aromatic sulfonates, isethionates, cocoamide monoethanolamine, cocoamidopropyl betaine, glucosides, decyl glucoside, lauryl glucoside, or a combination thereof.

Some additional suitable synthetic surfactants may include, for example, anionic, nonionic, cationic, zwitterionic, amphoteric surfactants, or combinations thereof. For example, the synthetic surfactant may include an anionic surfactant. The anionic surfactant may be branched or linear. Examples of suitable linear anionic surfactants may include ammonium lauryl sulfate, ammonium laureth sulfate, sodium lauryl sulfate, sodium laureth sulfate, potassium laureth sulfate, sodium lauryl sarcosinate, sodium lauroyl sarcosinate, sodium lauroyl isethionate, sodium cocoyl isethionate, lauryl sarcosine, cocoyl sarcosine, ammonium cocoyl sulfate, potassium lauryl sulfate, or combinations thereof.

The synthetic surfactant may further include sodium laureth(n) sulfate, hereinafter SLEnS, and/or sodium trideceth(n) sulfate, hereinafter STnS, where n defines the average moles of ethoxylation. The n for the SLEnS and/or the STnS may range from about 0 to about 8, from about 1 to about 3, about 2, or about 1. It will be understood that a material such as SLEnS or STnS may include a significant amount of molecules having no ethoxylate, 1 mole ethoxylate, 2 mole ethoxylate, 3 mole ethoxylate, and so on in a distribution which may be broad, narrow, or truncated. For example, SLE1S may include a significant amount of molecules which have no ethoxylate, 1 mole ethoxylate, 2 mole ethoxylate, 3 mole ethoxylate, and so on in a distribution which may be broad, narrow, or truncated and still include SLE1S where an average distribution may be about 1. Similarly, ST2S may include a significant amount of molecules which have no ethoxylate, 1 mole ethoxylate, 2 mole ethoxylate, 3 mole ethoxylate, and so on in a distribution which may be broad, narrow, or truncated and still comprise ST2S, where an average distribution may be about 2.

The synthetic surfactant may also include one or more branched anionic surfactants and monomethyl branched anionic surfactants such as sodium trideceth sulfate, sodium tridecyl sulfate, sodium C12-13 alkyl sulfate, C12-13 pareth sulfate, sodium C12-13 pareth-n sulfate, or combinations thereof.

As described above, the synthetic surfactant may include a nonionic surfactant. Nonionic surfactants for use in the composition may include, for example, those selected from the group consisting of alkyl glucosides, alkyl polyglucosides, polyhydroxy fatty acid amides, alkoxylated fatty acid esters, sucrose esters, amine oxides, or mixtures thereof.

The synthetic surfactant may further include a cationic surfactant. Cationic surfactants for use in a composition may include, but are not limited to, fatty amines, di-fatty quaternary amines, tri-fatty quaternary amines, imidazolinium quaternary amines, or combinations thereof.

The synthetic surfactant may further include an amphoteric surfactant. Suitable amphoteric surfactants may include those that are broadly described as derivatives of aliphatic secondary and tertiary amines, in which the aliphatic radical may be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition may include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. The surfactant included in the cleansing composition may include, for example, an amphoteric surfactant that may be selected from the group consisting of sodium lauroamphoacetate, sodium cocoamphoactetate, disodium lauroamphoacetate disodium cocodiamphoacetate, and mixtures thereof.

The synthetic surfactant may also include a zwitterionic surfactant. Suitable zwitterionic surfactants may include, for example, those that are broadly described as derivatives of aliphatic quaternary ammonium, phosphonium, and sulfonium compounds, in which the aliphatic radicals may be straight or branched chain, and wherein one aliphatic substituent contains from about 8 to about 18 carbon atoms and one contains an anionic group, e.g., carboxy, sulfonate, sulfate, phosphate, or phosphonate. In one example, the zwitterionic surfactant included in the composition may be one or more betaines such as cocoamidopropyl betaine.

The surfactant may also include a soap. The cleansing composition may include, for example, from about 20% to about 99.5%, from about 20% to about 75%, from about 20% to about 50%, or any combination thereof, by weight of the cleansing composition, of a soap.

The soap may include, for example, alkali metal or alkanol ammonium salts of alkane- or alkene monocarboxylic acids. Sodium, magnesium, potassium, calcium, mono-, di- and tri-ethanol ammonium cations, or combinations thereof, may be suitable. In one example, the soap comprises a sodium soap. In another example, the soap comprises a sodium soap and from about 1% to about 25% of at least one of ammonium, potassium, magnesium, and calcium soap. Suitable soaps may also include the well-known alkali metal salts of alkanoic or alkenoic acids having from about 12 to 22 carbon atoms, from about 12 to about 18 carbon atoms; or alkali metal carboxylates of alkyl or alkene hydrocarbons having from about 12 to about 22 carbon atoms.

The composition may also include soaps having a fatty acid distribution of coconut oil that may provide a lower end of a broad molecular weight range or a fatty acid distribution of peanut or rapeseed oil, or their hydrogenated derivatives, which may provide an upper end of the broad molecular weight range.

A soap in the cleansing composition may also include, for example, a fatty acid distribution of tallow and/or vegetable oil. The tallow may include fatty acid mixtures that typically have an approximate carbon chain length distribution of 2.5% C14, 29% C16, 23% C18, 2% palmitoleic, 41.5% oleic, and 3% linoleic. The tallow may also include other mixtures with similar distribution, such as the fatty acids derived from various animal tallows and/or lard. According to one example, the tallow may also be hardened (i.e., hydrogenated) to convert part or all of the unsaturated fatty acid moieties to saturated fatty acid moieties.

Suitable vegetable oil may be selected, for example, from the group consisting of palm oil, coconut oil, palm kernel oil, palm oil stearine, and hydrogenated rice bran oil, and mixtures thereof. In one example, the vegetable oil is selected from the group consisting of palm oil stearine, palm kernel oil, coconut oil, and combinations thereof. Suitable coconut oil may include a proportion of fatty acids having 12 carbon atoms or more of about 85%. Such a proportion may be greater when mixtures of coconut oil and fats such as tallow, palm oil, or non-tropical nut oils or fats are used where the principle chain lengths may be C16 and higher. According to one example, the soap included in the composition may be a sodium soap having a mixture of about 67-68% tallow, about 16-17 coconut oil, and about 2% glycerin, and about 14% water.

Soap is often made by a classic kettle boiling process or modern continuous soap manufacturing processes wherein natural fats and oils such as tallow or coconut oil or their equivalents may be saponified with an alkali metal hydroxide using procedures well known to those skilled in the art. Alternatively, the soaps may be made by neutralizing fatty acids such as lauric (C12), myristic (C14), palmitic (C16), or stearic (C18) acids with an alkali metal hydroxide or carbonate.

The cleansing composition also includes a hygroscopic fine, hygroscopic fiber, or a hygroscopic filament. The composition may include from about 3% to about 40%, by weight of the cleansing composition, of the fine, fiber, or filament. Additional acceptable levels may include from about 5% to about 35%, from about 10% to about 30%, or from about 15% to about 25%, by weight of the cleansing composition. A filament includes fibers and fines. A filament may include from about 1% to about 95%, by weight of the filament, of fines, and from about 99% to about 5%, by weight of the filament, of fibers; or from about 20% to about 90%, by weight of the filament, of fines, and from about 80% to about 10%, by weight of the filament, of fibers; or from about 50% to about 70%, by weight of the filament, of fines, and from about 50% to about 30%, by weight of the filament, of fibers. A filament may include a single type of fiber or multiple types of fibers. A filament may likewise include a single type of fine or multiple types of fines.

A fine, fiber, or filament may be, for example, natural, like from a plant or animal, modified natural, or a combination thereof. Examples of animal fines, fibers, or filaments may include wool, silk, and mixtures thereof. Plant fines, fibers, or filaments may, for example, be derived from a plant like wood, bark, oat, corn, cotton, cotton linters, flax, sisal, abaca, hemp, hesperaloe, jute, bamboo, bagasse, kudzu, corn, sorghum, gourd, agave, loofah, or mixtures thereof. One further example of a plant fine, fiber, or filament is a cellulose fine, fiber, or filament. Another exemplary fine, fiber, or filament may include a regenerated cellulose, like rayon.

Wood pulp fines, fibers, or filaments may include, for example, hardwood pulp or softwood pulp. Non-limiting examples of hardwood pulp filaments may include filaments derived from a fiber source selected from the group consisting of: Acacia, *Eucalyptus*, Maple, Oak, Aspen, Birch, Cottonwood, Alder, Ash, Cherry, Elm, Hickory, Poplar, Gum, Walnut, Locust, Sycamore, Beech, *Catalpa, Sassafras, Gmelina, Albizia*, Anthocephalus, and *Magnolia*. Non-limiting examples of softwood filaments may include filaments derived from a fiber source selected from the group consisting of: Pine, Spruce, Fir, Tamarack, Hemlock, Cypress, and Cedar.

A fine, fiber, or filament may also be synthetic. Some examples of suitable synthetic hygroscopic fibers, fines, or filaments may include nylon, polyester, polyvinyl alcohol, starch, starch derivatives, pectin, chitin, chitosan, cellulose derivatives such as methylcellulose, hydroxypropylcellulose, alkoxy celluloses, or a combination thereof.

The fibers will have a length and diameter. The fibers may have a length weighted average of about 6 cm or less, about 5 cm or less, about 2 cm or less, about 1 cm or less, about 8 mm or less, about 6 mm or less, about 4 mm or less, about 3 mm or less, about 2 mm or less, or about 1 mm or less. The fibers may have an average diameter of about 15 μm, about 20 μm, to about 35 μm, to about 40 μm, or any combination thereof. Fiber length may be used to help determine whether a particular fiber will require more energy to be mixed into a composition. For example, fiber lengths of greater than 1.0 mm were found to require more energy than desired to mix into a composition. Thus, fiber length values of less than 1.0 mm may be used where lower levels of energy are desired to incorporate the fiber into a composition.

The fibers may also have a kink angle. Fiber "kink" is a measurement of an abrupt change in the curvature of a fiber and is defined by the modified Kibblewhite's Kink Index. The angle of this abrupt change is defined as the "kink angle". Kink angle will affect the volume one fiber may occupy, essentially a fiber with a higher kink angle will occupy greater volume filling space more efficiently, this will affect the level of fiber needed to meet the desired compliance value. Exemplary fibers for use herein may have a kink angle or about 35 to about 65, about 40 to about 60, about 45 to about 55, or any combination thereof.

Another property of fibers is the shape factor. The shape factor describes the ratio of the fiber end to end distance as projected in space and the fiber length as measured along the fiber. For instance, a straight fiber will have a high shape factor, since the end to end distance approaches the value of the length along the fiber, while a curly fiber will have a low shape factor. Exemplary fibers for use herein may have a shape factor of about 70 to about 95.

One more property of a fiber is the curl value. The curl value describes the degree of non-straightness of a fiber. The STFI FiberMaster uses the following equation to calculate curl values: Curl value=[(100/Shape Factor)−1]*100. Exemplary fibers for use herein may have a curl value of about 10 to about 25.

Fines may have a greater surface area and are able to retain more solvent than higher aspect ratio fibers. Thus, fines may be used to help tune the cleansing composition or article to the desired compliance value. Fines may also be useful in formulating a composition that will be used up over time. Fines that are smaller than the opening in a substrate may be separated from the composition during use and exit the article through the substrate openings allowing the composition to become smaller during use and helping to signal the end of the life of the composition or article.

Fines may include both primary and secondary fines. Primary fines are naturally produced by the plant or animal source. Secondary fines are derived from fibers, meaning they start as fibers and then are processed into smaller pieces. Secondary fines may be derived, for example, from a natural fiber, like a plant fiber or animal fiber, a modified natural fiber, or a combination thereof. The fiber sources listed above are suitable for their primary fines or for their fibers to be converted into secondary fines and used herein. For example, a fine may include cellulose.

Some exemplary cellulose filaments and some of their properties and the properties of the included fibers are below:

| Water insoluble, natural filament | Fiber Length (mm) | Fiber Width (um) | Fiber Shape Factor | Fiber Curl Value | Fiber Kink Angle (deg) | Fiber Kink/mm | Fiber Aspect ratio | Britt Jar Fines (%) |
|---|---|---|---|---|---|---|---|---|
| Example HG1 | 2.776 | 33.5 | 84.5 | 18.3 | 55.79 | 0.29 | 82.9 | <3 |
| Example HG2 | 1.224 | 21.8 | 87.7 | 14.0 | 50.66 | 0.51 | 56.1 | ~20 |
| Example HG3 | 0.760 | 33.1 | 89.7 | 11.5 | 48.73 | 0.48 | 23.0 | 26.2 |
| Example HG4 | 0.403 | 28.4 | 84.7 | 18.1 | 54.56 | 0.95 | 14.2 | 54.3 |
| Example HG5 | 0.350 | 24.9 | 81.6 | 22.5 | 51.75 | 1.03 | 14.1 | 72.3 |
| Example HG6 | 0.287 | 29.5 | 80.5 | 24.2 | 49.59 | 1.23 | 9.7 | 88.6 |

Certain advantages and disadvantages are present with filament property selection. For example, the use of a filament with shorter fibers and a high fines content enables facile mixing with the surfactant system, however examples D6-D14 indicate that a higher wt % of such filaments may be needed to achieve a desired compliance. Conversely, filaments comprised of longer fibers and a lower wt % of fines may achieve desired compliance values at lower wt % in the composition. However, filaments with longer fibers and lower fines % may be more difficult to process and require more energy to mix with surfactant systems. Thus, these properties may also be considered when formulating a cleansing composition.

The composition may also include a solvent. Solvents for use herein may include, for example, water glycerin, dipropylene glycol, soybean oil, sucrose polyesters, or combinations thereof. Solvent may be present, for example, in an amount of about 5% to about 50%, about 10% to about 45%, about 15% to about 40%, about 20% to about 35%, or any combination thereof, by weight of the composition.

The composition disclosed herein may also include one or more additional ingredients such as polymers, gums, pluronics, inorganic salts such as zinc carbonate, antimicrobial agents such as zinc pyrithione, actives, brighteners, silica, moisturizers or benefit agents, and emulsifiers.

Test Methods a) Compliance Test

To measure the compliance of an article or composition prior to use, use a Texture Analyzer TA-XT2i (Texture Technologies Corp, NY, USA) equipped with at least a 5 kg load cell and a 0.75 inch ball probe at ambient conditions. Start the test with the probe above but not in contact with the article or composition and use a 2 gram trigger force to commence data collection for both force and distance (i.e., the zero depth point begins at 2 gram-force). Measure a compressive force (kg) at a compression rate of 1 mm/sec over a depth of 5 mm, ensuring that the personal care article or composition form a flat surface over contact area with the ball probe, near the center of the article or composition. Repeat measurements as needed (e.g., at least 3 times) to obtain a representative average value. To determine the compliance of the article or composition divide the maximum observed force (kg) by the maximum compression depth (5 mm). When using a 5 kg load cell some samples may exceed capacity, in this case the maximum compression depth will be less than the set depth of 5 mm, specified in the procedure. Compliance of the article includes a measured force contribution of both the composition and substrate components. If thick or lofty substrates are used such that the probe does not substantially engage a composition component, or if the composition is distributed heterogeneously, the test is performed in a region and to a depth such that the composition component is a substantial contributor to the measured compliance. For example, if thick or lofty substrates are used in an article, the trigger force may be increased until the zero point is within at least about 0.5 mm of the composition.

To measure compliance after a simulated bath/shower use a rotary tumbler (Lortone, Inc., Seattle, Wash., USA model 33B or equivalent) with 4 in. diameter by 4 in. deep cylindrical rubber housing having 825 cc internal volume. The housing revolves on the tumbler at 43 rpm. Obtain a supply of water at about 7.5 grains water hardness and conductivity between 100 to not more than 400 microSemens per centimeter (µS/cm) and heat in a reservoir beaker to 45° C. Maintain the water reservoir at the target temperature within 1 degree. Add 200.0 gm of water from the reservoir to the housing. Weigh an article or composition to obtain the initial weight, and add the article or composition to the housing. Seal the housing with its accompanying watertight lid and place the sealed housing onto the rotary tumbler for 3 minutes. Remove the housing, remove the housing lid, and retrieve the article or composition.

Hang the article or composition to dry under controlled temperature (20-25° C.) and relative humidity (50-60%) with no direct air circulation applied to articles. Take compliance measurements as a function of time. The first time point after simulated use should be no sooner than 5 min after the product has been removed from the rotary tumbler and hung to dry. The final time point may be taken at any point as desired or instructed. For example, the final point may be taken after 15 minutes of drying after one use; after 20 minutes of drying after one use; after 30 minutes of drying after one use; after 60 minutes of drying after one use; after 3 hours of drying after one use; after 5 hours of drying after one use; after 12 hours of drying after one use; after 25 hours of drying after one use; or after 48 hours of drying after one use. When measuring compliance after multiple simulated uses, dry the composition or article for 5 minutes between each simulated use and after the final simulated use, unless the drying time is otherwise specified. For example, to measure compliance after 2 simulated uses, the composition would be put through a simulated use cycle, dried for 5 minutes, put through the second simulated use cycle, dried for 5 minutes and then the compliance measured.

b) Dissolution Rate Test

Obtain a straight walled glass beaker having an inside diameter (i.d.) of 63 mm and an inside height of 87 mm, (e.g., Pyrex 250 mL (No. 1000) which are widely available). Pour 150 grams of distilled water at ambient temperature (75° F.) into the beaker and add a Teflon® coated magnetic stir bar to the beaker. (Note: The stir bar may be nominally 1.5 inches long×5/16 inches diameter, octagonally-shaped as viewed from the end, and may have a 1/16 in. wide molded pivot ring around its center where the diameter may be about 0.35 in.) Examples of a suitable stir bar can include Spinbar® magnetic stir bars available from Sigma Aldrich Corp. worldwide including Milwaukee, Wis., USA and at www.sigmaaldrich.com.

Measure and record the water conductivity of the water using a conductivity meter (e.g., a Mettler-Toledo Seven-Multi meter with InLab740 probe). (Note: The conductivity of the water should be about 2 microSemens/cm (uS/cm) or less to indicate a low level of dissolved solids present.) Remove the conductivity probe from the water and place the beaker onto a digitally controlled laboratory stirrer, for example Ika® Werke RET Control-visc available (e.g., from DivTech Equipment Co, Cincinnati, Ohio, USA). Center the beaker on the stirrer and turn the stirrer on to obtain a constant rotation speed of 500 rpm to establish a vortex in the water which measures about 3 cm depth from highest point of water at the beaker edge to lowest point of air at the vortex center. Observe the vortex from above to ensure the beaker is centered and that the magnetic stir bar is centered in the vortex. Weigh 1.0 grams of a composition pressed or formed together as a single unit and add it to the water near the beaker edge but not touching the beaker edge. Begin a timer and allow the water with composition to stir for 1 minute.

Turn off the stirrer. Insert the conductivity probe into the water in a location away from any undissolved material. Allow a measurement to stabilize for a few seconds and record conductivity. Turn the stirrer back on. Restart the timer as the digital readout passes 250 rpm. After an additional 1 minute has elapsed, turn off the stirrer and measure and record conductivity in the same manner as above. Turn the stirrer back on. Restart the timer as the digital readout passes 250 rpm. Repeat the process until a conductivity reading has been obtained every minute of stirring, for 5 minutes.

After taking a 5 minute conductivity reading, cap the beaker with a suitable watertight cover (e.g., plastic wrap). Shake the beaker vigorously for about 1 minute to dissolve remaining solids, using a vortex type agitator and/or mild heating in addition if necessary until all soluble components are observed dissolved by visible inspection. Cool the solution to less than 80° F. prior to the final measurement. Uncap the beaker, measure conductivity and record the value as a final conductivity.

Calculate the fractional dissolution ($f$) at each time point by the equation: $f$=(conductivity−water conductivity)/(final conductivity−water conductivity)

Calculate the dissolution half-life by fitting the fractional dissolution time series (6 points from 0 to 5 minutes) to a second order polynomial and calculate an interpolated or extrapolated result for a time at which a composition is half dissolved (i.e., $f$=0.5).

Dissolution half-life can be a measure of the propensity of a composition to resist solubilization by water. Bars of soap, for example, can have a dissolution half-life of 21.1 minutes (Ivory®™ Soap), exhibiting longevity and low consumption rate during use without a need for substrates as barriers to permeability. Liquid body wash can have a dissolution half-life of less than ½ minute and can be unsuitable as a composition for such articles.

c) Consumption Test

To measure the Consumption Rate of a personal care article or composition per simulated use as noted in this test method (not the Compliance test method), use a rotary tumbler (Lortone, Inc., Seattle, Wash., USA model 33B or equivalent) with a 4 in. diameter by 4 in. deep cylindrical rubber housing having 825 cc internal volume. The housing revolves on the tumbler at 43 rpm. Obtain a supply of tap water at about 7.5 grains water hardness and conductivity between 100 to not more than 400 microSemens per centimeter (μS/cm) and heat in a reservoir beaker to 45° C. Maintain the water supply at the target temperature within 1 degree for the test duration. Add 200.0 g water from the reservoir to the housing. Weigh an article or composition to obtain the initial weight, and add the article or composition to the housing. Seal the housing with its accompanying watertight lid and place the sealed housing onto the rotary tumbler for exactly 3 minutes. Remove the housing, remove the housing lid, and retrieve the article or composition. Stir the remaining water in the housing for a few seconds and measure its conductivity and temperature using a Mettler Toledo Seven multimeter with InLab 740 probe or equivalent. Dry the article or composition surface by pressing, not rubbing, using paper towels with light hand pressure for about 30 seconds, until it is dry to the touch and transfers no more visible water to a dry paper towel using the same pressure at any point on its surface or edges. If the article or composition transfers partially dissolved or dissolving components in addition to liquid water (e.g., if a composition is a conventional bar soap it may transfer paste-like material), the transferred components are to be removed and the article or composition is considered dry when visible transfer is no longer evident. Weigh the article or composition. Repeat this with the same article or composition five times. Subtract the weight after the fifth cycle from the weight after the second cycle and divide by 3 to obtain the consumption rate reported in units g/use.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EXAMPLES/COMBINATIONS

A. A method of making a personal care article, the method comprising:

placing a converting frame on an anvil plate assembly comprising an anvil plate;

placing at least one lower film on the anvil plate and the converting frame;

securing the at least one lower film within the converting frame;

placing a cleansing composition on the at least one lower film and within a perimeter of a centering guide on the anvil plate;

laying at least one upper substrate over the cleansing composition and the at least one lower substrate;

placing the converting frame and the anvil plate assembly on a target location of a heat press; and actuating the heat press to direct a heated seal plate onto the anvil plate, thereby contacting the at least one upper substrate to form a seal between the at least one upper substrate and the at least one lower substrate and thereby contain the cleansing composition therebetween.

B. The method of paragraph A, wherein the cleansing composition comprises:

a surfactant; and water insoluble hygroscopic fiber, fine, or filament; and wherein the cleansing composition is compliant.

C. The method of paragraph A, wherein the at least one lower substrate comprises two lower substrates and wherein the at least one upper substrate comprises two upper substrates.

D. The method of paragraph C, wherein the two upper substrates comprise:

a first upper film formed of polypropylene and polyethylene; and a second upper film formed of polyethylene.

E. The method of paragraph D, wherein the first upper film is positioned over the second upper film, such that the first upper film is an outermost layer of the personal care article and the second upper film separates the first upper film from the cleansing composition; and wherein polypropylene fibers of the first upper film comprise an outer surface of the first upper film.

F. The method of paragraph A, wherein securing the at least one lower substrate within the converting frame comprises clamping the at least one lower substrate between magnetic clamps of the converting frame.

G. The method of paragraph A, wherein the centering guide on the anvil plate is visible through the at least one lower substrate.

H. The method of paragraph A, wherein a first physical guide facilitates positioning of the converting frame and anvil plate assembly in the target location of the heat press.

I. The method of paragraph A, wherein the heated seal plate is heated to a temperature of from about 250° F. to about 300° F.

J. The method of paragraph A, wherein the heated seal plate comprises:

a base plate;

a wall extending perpendicularly from the base plate, wherein the base plate and wall define a seal plate cavity having a depth of from about 0.5 inches to about 2.5 inches; and a substrate-contacting portion on a surface of the wall opposite to and substantially in parallel with the base plate, the substrate-contacting portion comprising:

a substantially flat and continuous inner perimeter; and an outer perimeter comprising a plurality of knurls.

K. A method of making a personal care article, the method comprising:

placing a converting frame on an anvil plate assembly comprising an anvil plate;

placing at least one lower substrate on the anvil plate and the converting frame;

securing the at least one lower substrate within the converting frame;

placing a cleansing composition on the at least one lower substrate and within a perimeter of a centering guide on the anvil plate;

laying at least one upper substrate over the cleansing composition and the at least one lower substrate;

placing the converting frame and the anvil plate assembly on a target location of a heat press;

actuating the heat press to direct a heated seal plate onto the anvil plate, thereby contacting the at least one upper substrate to form a seal between the at least one upper substrate and the at least one lower substrate and thereby contain the cleansing composition between the at least one upper and lower substrates;

separating the anvil plate assembly from the converting frame;

placing the converting frame on a surface of a cutting press;

placing a die assembly comprising a die over the at least one upper substrate on the converting frame, such that the die is facing the surface of the cutting press; and actuating the cutting press to drive the die assembly onto the converting frame to cut excess portions of the at least one lower substrate and the at least one upper substrate at or outwardly adjacent to the seal to form the personal care article.

L. The method of paragraph K, wherein the cleansing composition is compliant.

M. The method of paragraph K, wherein the at least one upper substrate comprises:

a first upper film formed of polypropylene and polyethylene; and a second upper film formed of polyethylene; wherein the first upper film is positioned over the second upper film, such that the first upper film is an outermost layer of the personal care article and the second upper film separates the first upper film from the cleansing composition; and wherein polypropylene fibers of the first upper film comprise an outer surface of the first upper film.

N. The method of paragraph K, wherein a second physical guide facilitates placement of the die assembly on the converting frame.

O. The method of paragraph K, wherein the heated seal plate comprises:

a base plate;

a wall extending perpendicularly from the base plate, wherein the base plate and wall define a seal plate cavity having a depth from about 0.5 inches to about 2.5 inches; and a substrate-contacting portion on a surface of the wall opposite to and substantially in parallel with the base plate, the substrate-contacting portion comprising:

a substantially flat and continuous inner perimeter; and an outer perimeter comprising a plurality of knurls;

wherein the substantially flat and continuous inner perimeter contacts the at least one upper substrate to form the seal and the outer perimeter comprising a plurality of knurls contacts the at least one upper substrate to form a knurl bond outwardly adjacent to the seal; and wherein actuating the cutting press to drive the die assembly onto the converting frame comprises cutting the excess portions of the at least one lower substrate and the at least one upper substrate at the knurl bond.

P. The method of paragraph K, wherein actuating the cutting press to drive the die assembly onto the converting frame further comprises shaping the cleansing composition.

Q. The method of paragraph K, wherein the anvil plate is formed from a silicone having a hardness from about 40 A to about 100 A.

R. A method of making a personal care article, the method comprising:

unitizing a plodded extrudate cleansing composition to form a cleansing composition puck;

placing a converting frame on an anvil plate assembly comprising an anvil plate, placing at least one lower substrate on the anvil plate and the converting frame and securing the at least one lower substrate within the converting frame;

placing the cleansing composition puck on the at least one lower substrate and within a perimeter of a centering guide on the anvil plate, wherein the centering guide is substantially visible through the at least one lower substrate;

laying at least one upper substrate over the cleansing composition puck and the at least one lower substrate;

placing the converting frame and the anvil plate assembly on a target location of a heat press, wherein a first physical guide facilitates placement of the converting frame and the anvil plate assembly on the target location of the heat press;

actuating the heat press to direct a heated seal plate onto the anvil plate, thereby contacting the at least one upper substrate to form a seal between the at least one upper substrate and the at least one lower substrate and thereby contain the cleansing composition puck therebetween;

separating the anvil plate assembly from the converting frame;

placing the converting frame on a surface of a cutting press;

placing a die assembly comprising a die over the at least one upper substrate on the converting frame, such that the die is facing the surface of the cutting press, wherein a second physical guide facilitates placement of the die assembly on the converting frame; and actuating the cutting press to drive the die assembly onto the converting frame to cut excess portions of the at least one lower substrate and the at least one upper substrate at or outwardly adjacent to the seal to form the personal care article and to shape the cleansing composition therein; wherein the die and the die assembly define a die cavity having a depth that is less than a height of the cleansing composition prior to actuation of the cutting press.

S. The method of paragraph R, further comprising:

forming a loosely-amalgamated cleansing composition; and plodding the loosely-amalgamated cleansing composition.

T. The method of paragraph R, further comprising providing a vapor barrier for the personal care article and sealing the personal care article therein.

What is claimed is:

1. A method of making a personal care article, the method comprising:

placing a converting frame on an anvil plate assembly comprising an anvil plate;

placing at least one lower film on the anvil plate and the converting frame;

securing the at least one lower film within the converting frame;

placing a cleansing composition on the at least one lower film and within a perimeter of a centering guide on the anvil plate;

laying at least one upper substrate over the cleansing composition and the at least one lower substrate;

placing the converting frame and the anvil plate assembly on a target location of a heat press; and actuating the heat press to direct a heated seal plate onto the anvil plate, thereby contacting the at least one upper substrate to form a seal between the at least one upper substrate and the at least one lower substrate and thereby contain the cleansing composition therebetween.

2. The method of claim 1, wherein the cleansing composition comprises:

a surfactant; and water insoluble hygroscopic fiber, fine, or filament; and wherein the cleansing composition is compliant.

3. The method of claim 1, wherein the at least one lower substrate comprises two lower substrates and wherein the at least one upper substrate comprises two upper substrates.

4. The method of claim 3, wherein the two upper substrates comprise:

a first upper film formed of polypropylene and polyethylene; and a second upper film formed of polyethylene.

5. The method of claim 4, wherein the first upper film is positioned over the second upper film, such that the first upper film is an outermost layer of the personal care article and the second upper film separates the first upper film from the cleansing composition; and wherein polypropylene fibers of the first upper film comprise an outer surface of the first upper film.

6. The method of claim 1, wherein securing the at least one lower substrate within the converting frame comprises clamping the at least one lower substrate between magnetic clamps of the converting frame.

7. The method of claim 1, wherein the centering guide on the anvil plate is visible through the at least one lower substrate.

8. The method of claim 1, wherein a first physical guide facilitates positioning of the converting frame and anvil plate assembly in the target location of the heat press.

9. The method of claim 1, wherein the heated seal plate is heated to a temperature of from about 250° F. to about 300° F.

10. The method of claim 1, wherein the heated seal plate comprises:

a base plate;

a wall extending perpendicularly from the base plate, wherein the base plate and wall define a seal plate cavity having a depth of from about 0.5 inches to about 2.5 inches; and a substrate-contacting portion on a surface of the wall opposite to and substantially in parallel with the base plate, the substrate-contacting portion comprising:

a substantially flat and continuous inner perimeter; and an outer perimeter comprising a plurality of knurls.

11. A method of making a personal care article, the method comprising:

placing a converting frame on an anvil plate assembly comprising an anvil plate;

placing at least one lower substrate on the anvil plate and the converting frame;

securing the at least one lower substrate within the converting frame;

placing a cleansing composition on the at least one lower substrate and within a perimeter of a centering guide on the anvil plate;

laying at least one upper substrate over the cleansing composition and the at least one lower substrate;

placing the converting frame and the anvil plate assembly on a target location of a heat press;

actuating the heat press to direct a heated seal plate onto the anvil plate, thereby contacting the at least one upper substrate to form a seal between the at least one upper substrate and the at least one lower substrate and thereby contain the cleansing composition between the at least one upper and lower substrates;

separating the anvil plate assembly from the converting frame;

placing the converting frame on a surface of a cutting press;

placing a die assembly comprising a die over the at least one upper substrate on the converting frame, such that the die is facing the surface of the cutting press; and actuating the cutting press to drive the die assembly onto the converting frame to cut excess portions of the at least one lower substrate and the at least one upper substrate at or outwardly adjacent to the seal to form the personal care article.

12. The method of claim 11, wherein the cleansing composition is compliant.

13. The method of claim 11, wherein the at least one upper substrate comprises:
a first upper film formed of polypropylene and polyethylene; and
a second upper film formed of polyethylene; wherein the first upper film is positioned over the second upper film, such that the first upper film is an outermost layer of the personal care article and the second upper film separates the first upper film from the cleansing composition; and
wherein polypropylene fibers of the first upper film comprise an outer surface of the first upper film.

14. The method of claim 11, wherein a second physical guide facilitates placement of the die assembly on the converting frame.

15. The method of claim 11, wherein the heated seal plate comprises:
a base plate;
a wall extending perpendicularly from the base plate, wherein the base plate and wall define a seal plate cavity having a depth from about 0.5 inches to about 2.5 inches; and
a substrate-contacting portion on a surface of the wall opposite to and substantially in parallel with the base plate, the substrate-contacting portion comprising:
a substantially flat and continuous inner perimeter; and
an outer perimeter comprising a plurality of knurls;
wherein the substantially flat and continuous inner perimeter contacts the at least one upper substrate to form the seal and the outer perimeter comprising a plurality of knurls contacts the at least one upper substrate to form a knurl bond outwardly adjacent to the seal; and
wherein actuating the cutting press to drive the die assembly onto the converting frame comprises cutting the excess portions of the at least one lower substrate and the at least one upper substrate at the knurl bond.

16. The method of claim 11, wherein actuating the cutting press to drive the die assembly onto the converting frame further comprises shaping the cleansing composition.

17. The method of claim 11, wherein the anvil plate is formed from a silicone having a hardness from about 40 A to about 100 A.

18. A method of making a personal care article, the method comprising:
unitizing a plodded extrudate cleansing composition to form a cleansing composition puck;
placing a converting frame on an anvil plate assembly comprising an anvil plate, placing at least one lower substrate on the anvil plate and the converting frame and securing the at least one lower substrate within the converting frame;
placing the cleansing composition puck on the at least one lower substrate and within a perimeter of a centering guide on the anvil plate, wherein the centering guide is substantially visible through the at least one lower substrate;
laying at least one upper substrate over the cleansing composition puck and the at least one lower substrate;
placing the converting frame and the anvil plate assembly on a target location of a heat press, wherein a first physical guide facilitates placement of the converting frame and the anvil plate assembly on the target location of the heat press;
actuating the heat press to direct a heated seal plate onto the anvil plate, thereby contacting the at least one upper substrate to form a seal between the at least one upper substrate and the at least one lower substrate and thereby contain the cleansing composition puck therebetween;
separating the anvil plate assembly from the converting frame;
placing the converting frame on a surface of a cutting press;
placing a die assembly comprising a die over the at least one upper substrate on the converting frame, such that the die is facing the surface of the cutting press, wherein a second physical guide facilitates placement of the die assembly on the converting frame; and
actuating the cutting press to drive the die assembly onto the converting frame to cut excess portions of the at least one lower substrate and the at least one upper substrate at or outwardly adjacent to the seal to form the personal care article and to shape the cleansing composition therein; wherein the die and the die assembly define a die cavity having a depth that is less than a height of the cleansing composition prior to actuation of the cutting press.

19. The method of claim 18, further comprising:
forming a loosely-amalgamated cleansing composition; and
plodding the loosely-amalgamated cleansing composition.

20. The method of claim 18, further comprising providing a vapor barrier for the personal care article and sealing the personal care article therein.

* * * * *